(12) United States Patent
Hestad et al.

(10) Patent No.: US 8,137,356 B2
(45) Date of Patent: Mar. 20, 2012

(54) FLEXIBLE GUIDE FOR INSERTION OF A VERTEBRAL STABILIZATION SYSTEM

(75) Inventors: Hugh D. Hestad, Edina, MN (US); Zachary M. Hoffman, Bloomington, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 519 days.

(21) Appl. No.: 12/345,238

(22) Filed: Dec. 29, 2008

(65) Prior Publication Data

US 2010/0168803 A1 Jul. 1, 2010

(51) Int. Cl.
*A61B 17/70* (2006.01)
(52) U.S. Cl. .................. 606/86 A; 606/99; 606/279
(58) Field of Classification Search .............. 606/96, 606/99, 86 A, 104, 246, 279
See application file for complete search history.

(56) References Cited

U.S. PATENT DOCUMENTS

| | | | |
|---|---|---|---|
| 4,743,260 A | 5/1988 | Burton | |
| 5,176,708 A | 1/1993 | Frey et al. | |
| 5,375,823 A | 12/1994 | Navas | |
| 5,540,688 A | 7/1996 | Navas | |
| 5,562,660 A | 10/1996 | Grob | |
| 5,725,582 A | 3/1998 | Bevan et al. | |
| 5,782,831 A | 7/1998 | Sherman et al. | |
| RE36,221 E | 6/1999 | Breard et al. | |
| 6,248,106 B1 | 6/2001 | Ferree | |
| 6,290,700 B1 | 9/2001 | Schmotzer | |
| 6,610,079 B1 | 8/2003 | Li et al. | |
| 6,802,844 B2 | 10/2004 | Ferree | |
| 6,986,771 B2 | 1/2006 | Paul et al. | |
| 6,989,011 B2 | 1/2006 | Paul et al. | |
| 7,008,424 B2 | 3/2006 | Teitelbaum | |
| 7,029,475 B2 | 4/2006 | Panjabi | |
| 7,137,985 B2 | 11/2006 | Jahng | |
| 7,326,210 B2 | 2/2008 | Jahng et al. | |
| 7,491,208 B2 * | 2/2009 | Pond et al. .................. 606/104 |
| 2002/0035366 A1 | 3/2002 | Walder et al. | |
| 2004/0049189 A1 | 3/2004 | Le Couedic et al. | |
| 2004/0215191 A1 | 10/2004 | Kitchen | |

(Continued)

FOREIGN PATENT DOCUMENTS

EP 0516567 A1 12/1992

(Continued)

OTHER PUBLICATIONS

Davis, Regmald J. and Maxwell, James H., "Dynesys LIS surgical technique," Dynesys LIS Less Invasive Surgery, The Dynamic Stabilization System, 2005, Zimmer SPine, Inc., 24 pgs.

*Primary Examiner* — Eduardo C Robert
*Assistant Examiner* — Christina Negrelli
(74) *Attorney, Agent, or Firm* — Seager Tufte & Wickhem LLC

(57) ABSTRACT

An installation system for installing a vertebral stabilization system. The system includes an implant guide and an insert. The implant guide includes a handle and a shaft extending from the handle. The distal end of the shaft is configured for engagement with a head portion of a vertebral anchor. The shaft has flexibility characteristics allowing the shaft to flexibly bend between a first configuration and a second configuration. The insert is slidably disposed along the shaft of the implant guide. The insert inhibits the shaft from bending from the second configuration to the first configuration.

16 Claims, 30 Drawing Sheets

U.S. PATENT DOCUMENTS

| | | |
|---|---|---|
| 2004/0225289 A1 | 11/2004 | Biedermann et al. |
| 2005/0010220 A1 | 1/2005 | Casutt et al. |
| 2005/0056979 A1 | 3/2005 | Studer et al. |
| 2005/0065516 A1 | 3/2005 | Jahng |
| 2005/0085815 A1 | 4/2005 | Harms et al. |
| 2005/0096652 A1 | 5/2005 | Burton |
| 2005/0124991 A1 | 6/2005 | Jahng |
| 2005/0143737 A1 | 6/2005 | Pafford et al. |
| 2005/0154390 A1 | 7/2005 | Biedermann et al. |
| 2005/0177157 A1 | 8/2005 | Jahng |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203517 A1 | 9/2005 | Jahng et al. |
| 2005/0277922 A1 | 12/2005 | Trieu et al. |
| 2006/0106380 A1 | 5/2006 | Colleran |
| 2006/0111715 A1 | 5/2006 | Jackson |
| 2006/0142758 A1 | 6/2006 | Petit |
| 2006/0173454 A1 | 8/2006 | Spitler et al. |
| 2006/0195093 A1 | 8/2006 | Jahng |
| 2006/0200129 A1 | 9/2006 | Denti |
| 2006/0212033 A1 | 9/2006 | Rothman et al. |
| 2006/0229615 A1 | 10/2006 | Abdou |
| 2006/0247638 A1 | 11/2006 | Trieu et al. |
| 2007/0005062 A1 | 1/2007 | Lange et al. |
| 2007/0005063 A1 | 1/2007 | Bruneau et al. |
| 2007/0016200 A1 | 1/2007 | Jackson |
| 2007/0055244 A1 | 3/2007 | Jackson |
| 2007/0100341 A1 | 5/2007 | Reglos et al. |
| 2007/0106123 A1 | 5/2007 | Gorek et al. |
| 2007/0118119 A1 | 5/2007 | Hestad |
| 2007/0129729 A1 | 6/2007 | Petit et al. |
| 2007/0198088 A1 | 8/2007 | Biedermann et al. |
| 2007/0225710 A1 | 9/2007 | Jahng et al. |
| 2007/0233075 A1 | 10/2007 | Dawson |
| 2007/0233087 A1 | 10/2007 | Schlapfer |
| 2007/0233095 A1 | 10/2007 | Schlaepfer |
| 2007/0239158 A1 | 10/2007 | Trieu et al. |
| 2007/0270821 A1 | 11/2007 | Trieu et al. |
| 2007/0270860 A1 | 11/2007 | Jackson |
| 2007/0293862 A1 | 12/2007 | Jackson |
| 2008/0009863 A1 | 1/2008 | Bond et al. |
| 2008/0021459 A1 | 1/2008 | Lim |
| 2008/0021465 A1 | 1/2008 | Shadduck et al. |
| 2008/0039843 A1 | 2/2008 | Abdou |
| 2008/0091213 A1 | 4/2008 | Jackson |
| 2008/0140076 A1 | 6/2008 | Jackson |
| 2008/0147122 A1 | 6/2008 | Jackson |
| 2008/0161857 A1* | 7/2008 | Hestad et al. .................. 606/264 |
| 2008/0177317 A1 | 7/2008 | Jackson |
| 2008/0183216 A1 | 7/2008 | Jackson |
| 2008/0195153 A1 | 8/2008 | Thompson |
| 2008/0234737 A1 | 9/2008 | Boschert |
| 2008/0234738 A1 | 9/2008 | Zylber et al. |
| 2008/0234744 A1 | 9/2008 | Zylber et al. |
| 2008/0262551 A1 | 10/2008 | Rice et al. |
| 2008/0275456 A1 | 11/2008 | Vonwiller et al. |
| 2008/0294198 A1 | 11/2008 | Jackson |
| 2008/0300633 A1 | 12/2008 | Jackson |
| 2008/0319486 A1 | 12/2008 | Hestad et al. |
| 2009/0005817 A1 | 1/2009 | Friedrich et al. |
| 2009/0012562 A1 | 1/2009 | Hestad et al. |
| 2009/0036924 A1 | 2/2009 | Egli et al. |
| 2009/0082815 A1 | 3/2009 | Zylber et al. |
| 2009/0093846 A1 | 4/2009 | Hestad |
| 2009/0099606 A1 | 4/2009 | Hestad et al. |

FOREIGN PATENT DOCUMENTS

| | | |
|---|---|---|
| EP | 0669109 A1 | 8/1995 |
| EP | 0669109 B1 | 8/1995 |
| EP | 1523949 A1 | 4/2005 |
| EP | 1523949 B1 | 4/2005 |
| EP | 1719468 A1 | 11/2006 |
| FR | 2715057 A1 | 7/1995 |
| FR | 2775583 A1 | 9/1999 |
| FR | 2844180 A1 | 3/2004 |
| FR | 2867057 A1 | 9/2005 |
| NL | 7610576 | 3/1978 |
| WO | 9519149 | 7/1995 |
| WO | 9905980 A1 | 2/1999 |
| WO | 9944527 A1 | 9/1999 |
| WO | 2004024011 A1 | 3/2004 |
| WO | 2004089244 A2 | 10/2004 |
| WO | 2005037110 A2 | 4/2005 |
| WO | 2005037150 A1 | 4/2005 |
| WO | 2005087121 A1 | 9/2005 |
| WO | 2006066685 A1 | 6/2006 |
| WO | 2007044705 A2 | 4/2007 |
| WO | 2007044795 A2 | 4/2007 |
| WO | 2007087476 A1 | 8/2007 |
| WO | 2008006098 A2 | 1/2008 |
| WO | 2008013892 A2 | 1/2008 |
| WO | 2008021319 A2 | 2/2008 |
| WO | 2008034130 A2 | 3/2008 |
| WO | 20080134703 A2 | 11/2008 |

* cited by examiner

FLEXIBLE GUIDE FOR INSERTION OF A VERTEBRAL STABILIZATION SYSTEM

TECHNICAL FIELD

The disclosure is directed to surgical methods and associated installation systems for spinal stabilization. More particularly, the disclosure is directed to a flexible guide and one or more inserts that facilitate installation of a flexible spinal stabilization system into a patient.

BACKGROUND

The spinal column of a patient includes a plurality of vertebrae linked to one another by facet joints and an intervertebral disc located between adjacent vertebrae. The facet joints and intervertebral disc allow one vertebra to move relative to an adjacent vertebra, providing the spinal column a range of motion. Diseased, degenerated, damaged, or otherwise impaired facet joints and/or intervertebral discs may cause the patient to experience pain or discomfort and/or loss of motion, thus prompting surgery to alleviate the pain and/or assist motion of the spinal column.

Methods of treating spinal column disorders include installing a spinal stabilization system to stabilize a segment of the spinal column. One conventional spinal stabilization system includes securing a rigid rod between two or more vertebrae with pedicle screws or other vertebral anchors. Another technique utilizes a less rigid connecting element to provide a more dynamic stabilization of the affected segment of the spinal column. One example of a dynamic stabilization system is the DYNESYS system available from Zimmer Spine, Inc. of Minneapolis, Minn. Such dynamic stabilization systems may include a flexible, tubular spacer positioned between pedicle screws installed between adjacent vertebrae. The spacer is positioned between the pedicle screws and a flexible cord is threaded through the spacer. The flexible cord is secured to the heads of the pedicle screws by set screws, thereby retaining the spacer between the pedicle screws while cooperating with the spacer to permit mobility of the spine.

Some surgical situations may make installation of a spinal stabilization system using known installation systems difficult and/or impracticable in some circumstances. For instance, in a surgical situation in which pedicle screws are anchored to adjacent vertebrae in a converging orientation, it may be difficult to implant a stabilization system between the converging pedicle screws using known installation systems. Additionally and/or alternatively, it may be desirable to facilitate docking of an installation tool with a pedicle screw and/or make alterations to an installation tool without undocking the tool from the pedicle screw. Therefore, alternative systems and associated methods for installing a vertebral stabilization system are desirable.

SUMMARY

The disclosure is directed to several alternative apparatus, systems and methods for installation of a vertebral stabilization system.

Accordingly, one illustrative embodiment is a system for implanting a spinal stabilization system. The system includes an implant guide and an insert. The implant guide includes a handle and a shaft extending from the handle. The distal end of the shaft is configured for engagement with a head portion of a vertebral anchor. The shaft has flexibility characteristics allowing the shaft to flexibly bend between a first configuration and a second configuration. The insert is slidably disposed along the shaft of the implant guide. The insert inhibits the shaft from bending from the second configuration to the first configuration.

Another illustrative embodiment is a system for implantation of a spinal stabilization system. The system includes an implant guide and an insert. The implant guide includes a handle and a shaft extending from the handle. The distal end of the shaft is configured for engagement with a head portion of a vertebral anchor. The shaft is flexible away from an equilibrium configuration. The insert is slidably disposed along the shaft of the implant guide. The insert includes a curved shaft portion having a curvature. The curved shaft portion of the insert subjects the shaft of the implant guide into a curved configuration away from the equilibrium configuration.

Still another illustrative embodiment is a system for use in the installation of a spinal stabilization system. The system includes a vertebral anchor, an implant guide, and a docking member. The vertebral anchor includes a head portion and a shaft portion. The head portion includes a threaded opening extending into the head portion from an upper end of the head portion. The implant guide includes a handle and a shaft extending from the handle. The distal end of the shaft is configured for engagement with the head portion of the vertebral anchor. The docking member is inserted along the shaft of the implant guide. A distal end of the docking member includes a post sized for insertion into the threaded opening of the head portion of the vertebral anchor. The shaft is slidable relative to the docking member such that in a first configuration the distal end of the shaft is disengaged from the head portion of the vertebral anchor while the post of the docking member is positioned in the threaded opening of the vertebral anchor, and in a second configuration the distal end of the shaft is engaged with the head portion of the vertebral anchor while the post of the docking member is positioned in the threaded opening of the vertebral anchor.

Yet another illustrative embodiment is a method of engaging a vertebral anchor with an implant guide. The method comprises providing a docking member having a proximal portion and a distal portion. The distal portion of the docking member includes a post. The post of the docking member is inserted into a threaded opening of a head portion of a vertebral anchor implanted into a bone of a spinal column. With the post inserted into the threaded opening, an implant guide is slid along the docking member toward the head portion of the vertebral anchor. The distal end of the implant guide is engaged with the head portion of the vertebral anchor with the post inserted into the threaded opening. The post of the docking member is withdrawn from the threaded opening of the head portion of the vertebral anchor once the distal end of the implant guide is engaged with the head portion of the vertebral anchor.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
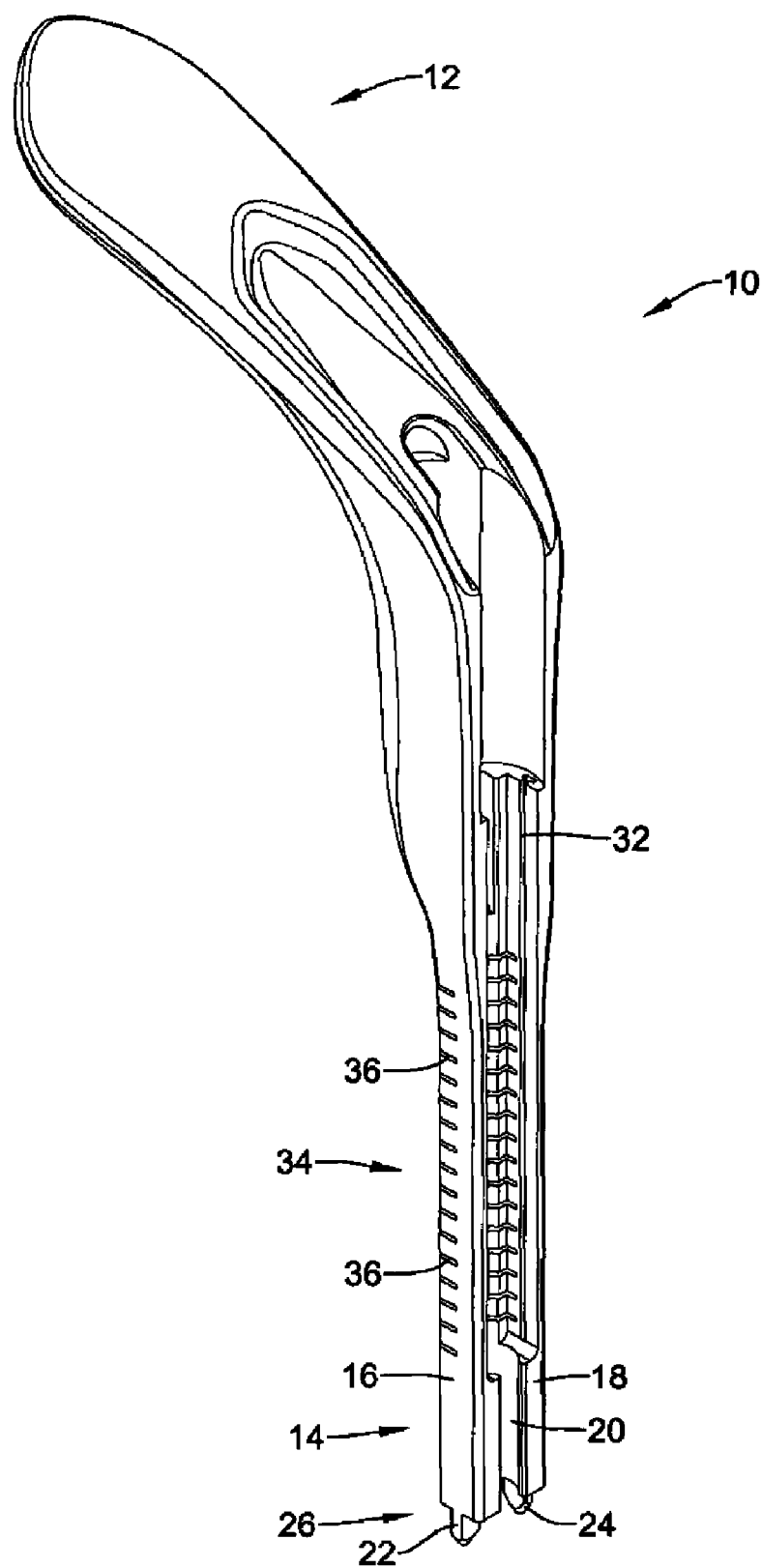
FIG. 1 is a perspective view of an illustrative implant guide.
Figure 1A:
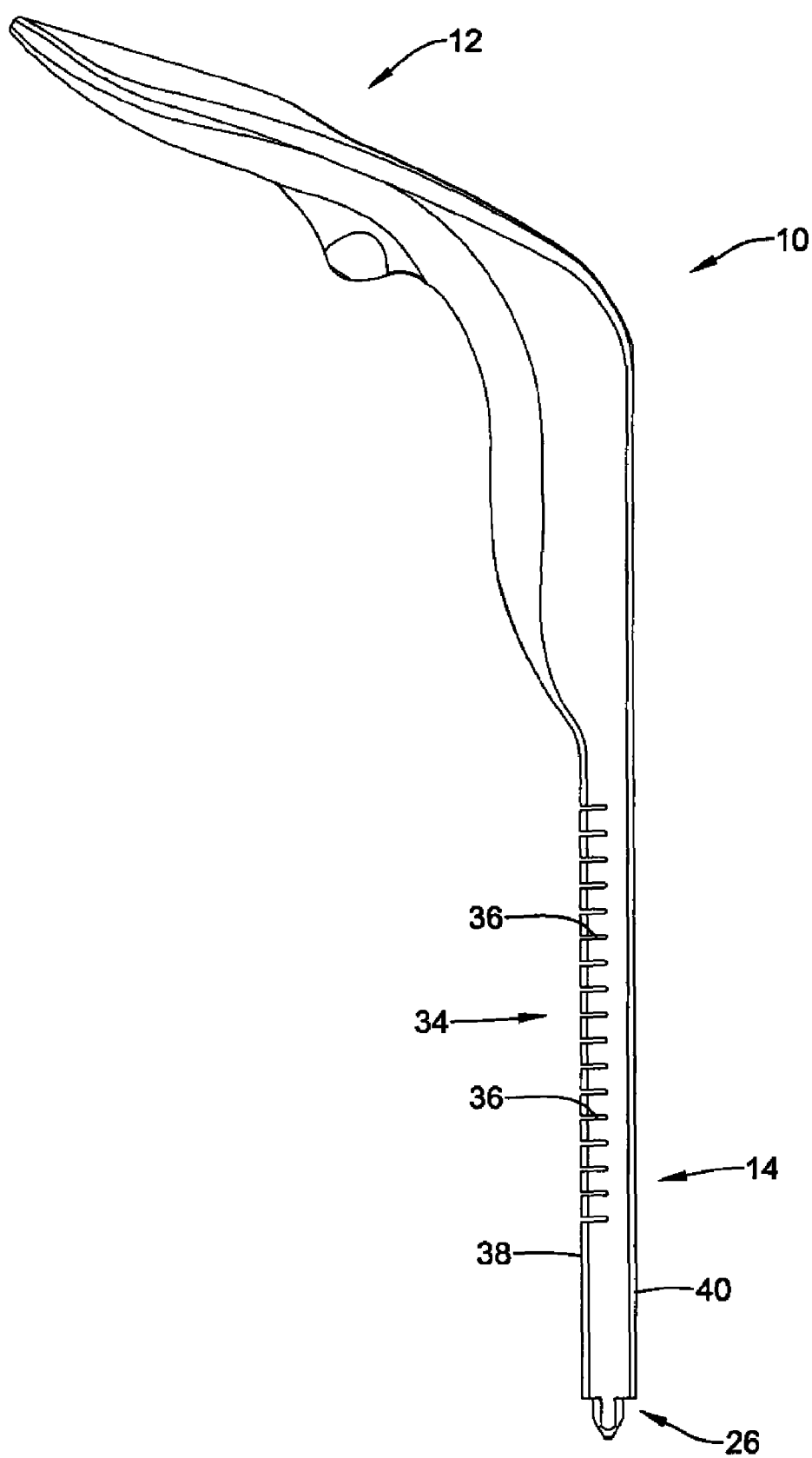
FIG. 1A is a side view of the implant guide of FIG. 1.
Figure 1B:
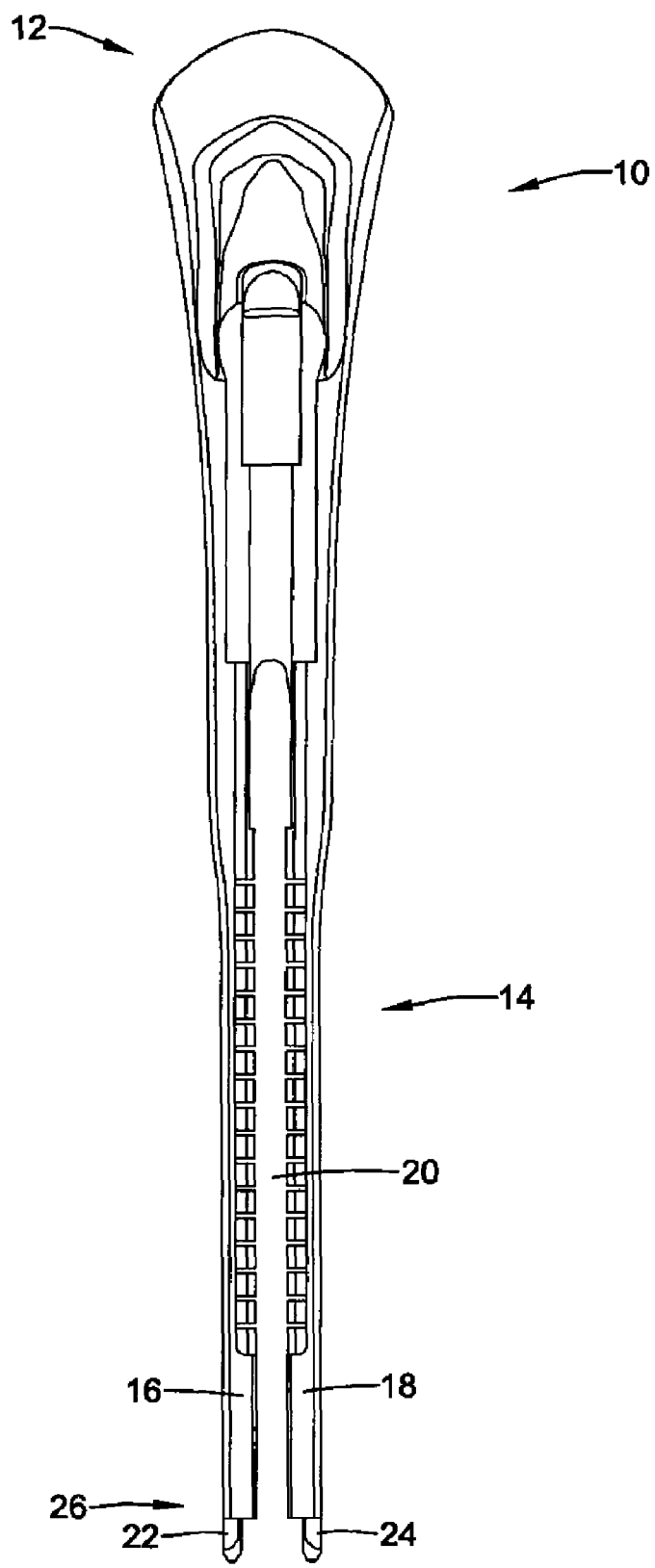
FIG. 1B is a front view of the implant guide of FIG. 1.
Figure 1C:
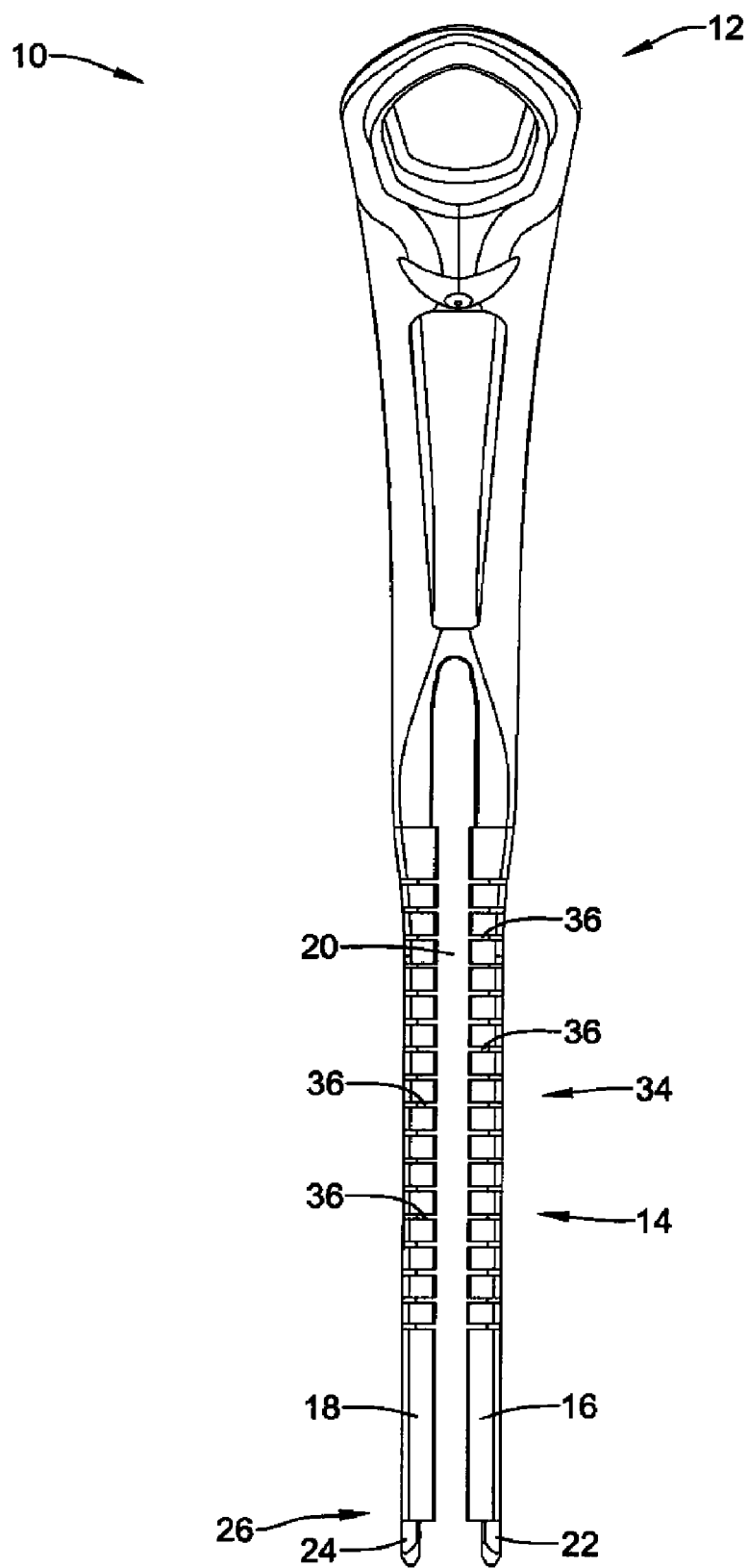
FIG. 1C is a back view of the implant guide of FIG. 1.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now referring to the drawings, an exemplary implant guide 10 for use in an installation procedure for installing a spinal stabilization system is illustrated in FIGS. 1, 1A, 1B and 1C. The implant guide 10 includes a handle 12 and a shaft 14 extending distally from the handle 12. In some embodiments, the shaft 14 may include a first leg 16 and a second leg 18. The first leg 16 may be spaced from the second leg 18, providing a channel 20 between the first leg 16 and the second leg 18. The channel 20 may extend from a proximal portion of the shaft 14 to the distal end of the shaft 14, separating the first leg 16 and the second leg 18 at the distal end of the shaft 14.

The distal end 26 of the shaft 14 of the implant guide 10 may be configured to engage with the head portion of a vertebral anchor, such as the head portion of a pedicle screw. Some suitable engagement configurations are shown and described in U.S. patent application Ser. Nos. 11/539,287, 11/737,151, 11/743,481, and 12/025,984, the disclosures of which are incorporated herein by reference.

As shown in the figures, the engagement configuration may include a first engagement member, such as the first tang or projection 22, extending from the distal end of the first leg 16 and/or a second engagement member, such as the second tang or projection 24, extending from the distal end of the second leg 18. As will be discussed further herein, the first and second tangs 22, 24 may be configured to engage with first and second engagement portions of a vertebral anchor, such as grooves, channels, notches or other openings in the head portion of a vertebral anchor.

The shaft 14 of the implant guide 10 may include one or more engagement features which may interact with one or more complementary engagement features of an insert configured to be used with the implant guide 10 during a medical procedure. For instance, the first leg 16 of the shaft 14 may include an engagement feature which interacts with an engagement feature of an insert which may be slidably disposed along the shaft 14 and/or the second leg 18 of the shaft 14 may include an engagement feature which interacts with an engagement feature of an insert which may be slidably disposed along the shaft 14.

For instance, the first leg 16 of the shaft 14 may include a first slot 30 (shown in FIG. 4A) extending from a proximal portion of the shaft 14 toward a distal portion of the shaft 14. The second leg 18 of the shaft 14 may include a second slot 32 extending from a proximal portion of the shaft 14 toward a distal portion of the shaft 14. In some embodiments, the first slot 30 and/or the second slot 32 may be open at the proximal end of the slot 30, 32 to allow insertion of a portion of another component, such as an engagement feature of an insert into the slot 30, 32. In some embodiments, the first slot 30 and/or the second slot 32 may be closed at the distal end of the slot 30, 32 to provide a stop so as to prevent the exiting of a portion of another component, such as an engagement feature of an insert out the distal end of the slot 30, 32.

In some embodiments, the first and second slots 30, 32 may have a T-shaped configuration, a trapezoidal configuration, or other desired configuration preventing disengagement of a portion of another component, such as an engagement feature of an insert, in a lateral direction perpendicular to the longitudinal axis of the first and second slots 30, 32.

A portion of the length of the shaft 14 may include flexibility characteristics 34 providing the shaft 14 with the ability to flexibly bend from a first configuration to a second configuration. For example, the shaft 14 may include a plurality of cuts or slots 36 providing the shaft 14 with a degree of flexibility. In some embodiments, the cuts 36 may be formed in the shaft 14 in a direction transverse to the longitudinal axis of the shaft 14. However, other arrangements and/or orientations of the cuts 36 are contemplated to provide the shaft 14 with a desired degree of flexibility. The cuts 36 may extend into a portion of the first leg 16 and/or the second leg 18 of the shaft 14. In some embodiments, the cuts 36 may extend into the legs 16, 18 of the shaft 14 from the lower surface 38 toward the upper surface 40 of the shaft 14. The cuts 36 may allow the shaft 14 to be flexibly bent from a straight configuration to a curved configuration, from a curved configuration to another curved configuration, or from a curved configuration to a straight configuration.

The implant guide 10, or at least the flexible shaft portion of the implant guide 10, may be formed of any desired material which may independently and/or in conjunction with the cuts 36 provide the shaft 14 with a degree of bending flexibility. Some materials include polymeric materials such as polypropylene, polyethylene, polycarbonate, polycarbonate urethane (PCU), silicone, polyetheretherketone (PEEK), copolymers, mixtures or blends thereof, or another suitable material. Additional suitable materials include biocompatible metals, such as stainless steel, titanium, and alloys thereof, or other suitable metallic materials.

Figure 2:
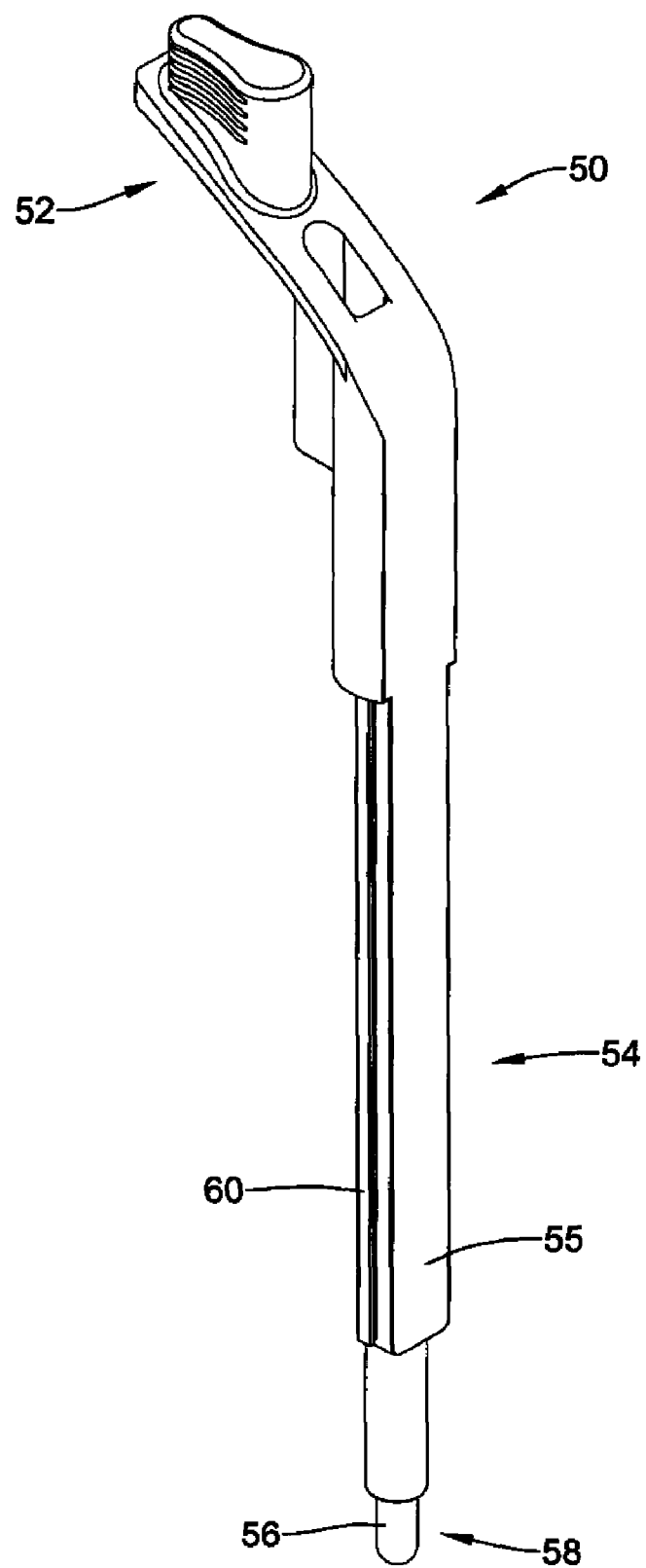
FIG. 2 is a perspective view of an illustrative docking member for use with the implant guide of FIG. 1.
Figure 2A:
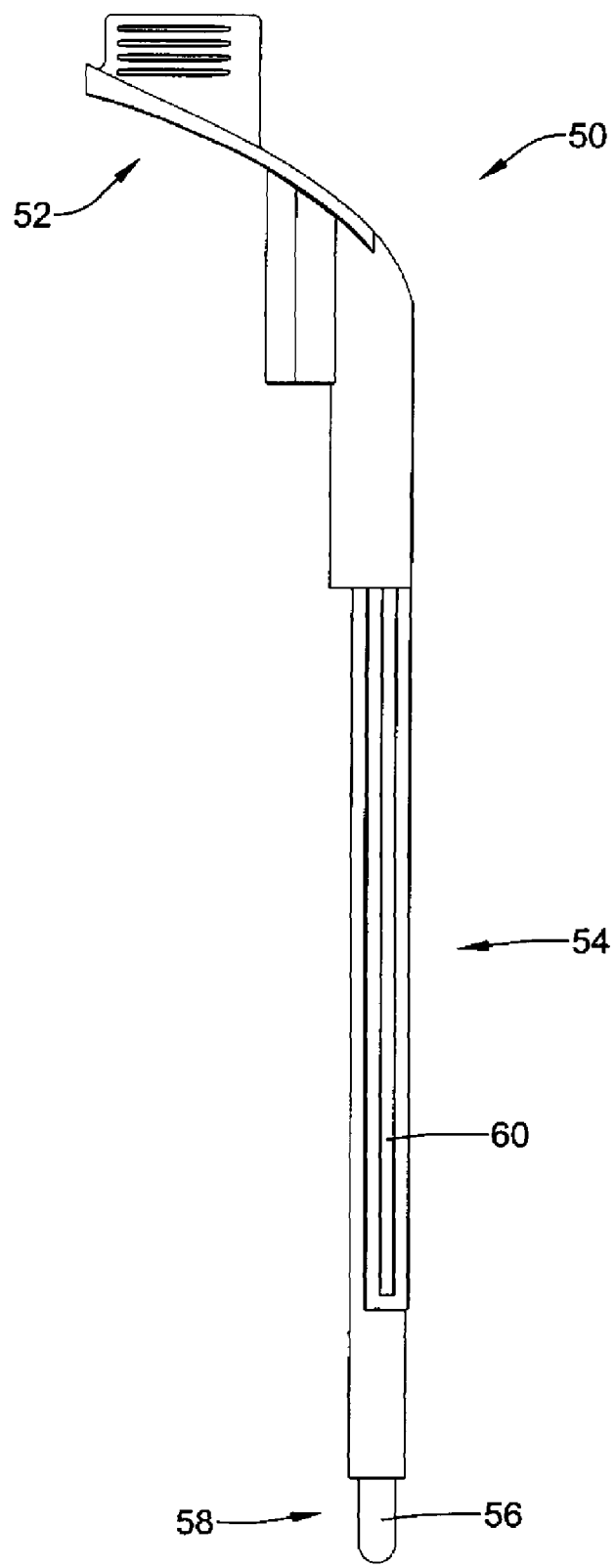
FIG. 2A is a side view of the docking member of FIG. 2.
Figure 2B:
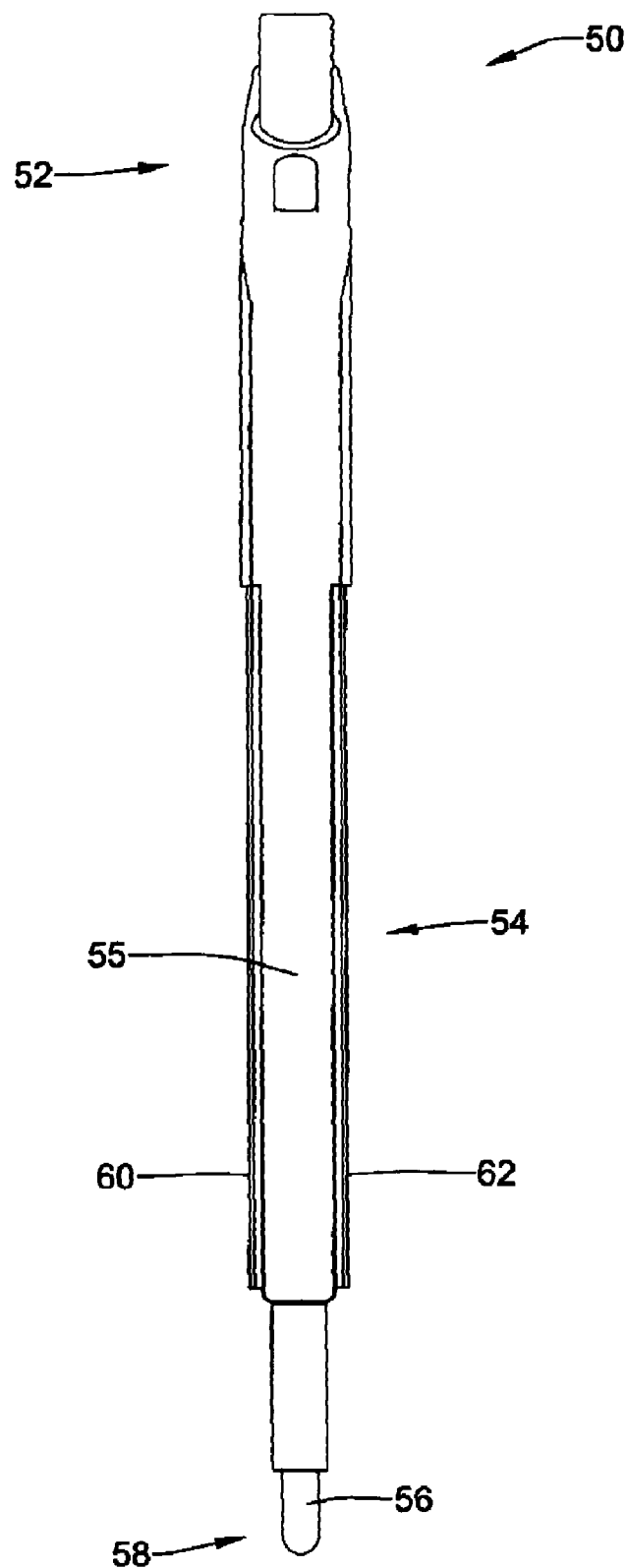
FIG. 2B is a front view of the docking member of FIG. 2.

An insert, in the form of a docking member 50 which may be used in association with the implant guide 10 of FIG. 1 is illustrated in FIGS. 2, 2A and 2B. The docking member 50 may include a handle 52 and a shaft 54 extending distally from the handle 52. The shaft 54 may include a post 56 located at the distal end 58 of the shaft 54. The post 56 may be a separate component attached to the shaft 54, or the post 56 may be a unitary continuation of the shaft 54. In some embodiments, the post 56 may be a cylindrical member having a spherical distal end, as shown in FIG. 2. In other embodiments, the post 56 may have a different shape if desired.

The shaft 54 of the docking member 50 may include one or more engagement features which may interact with one or more complementary engagement features of the shaft 14 of the implant guide 10. For instance, the shaft 54 of the docking member 50 may include an engagement feature which interacts with an engagement feature of the first leg 16 of the implant guide 10 and an engagement feature which interacts with an engagement feature of the second leg 18 of the implant guide 10. The interaction of the complementary engagement features of the implant guide 10 and the docking member 50 may allow relative movement between the docking member 50 and the implant guide 10. For instance, the complementary engagement features may allow sliding movement of the docking member 50 relative to the implant guide 10.

For instance, the shaft 54 of the docking member 50 may include a first rail 60 extending along a first side of the shaft 54 and/or a second rail 62 extending along a second side of the shaft 54 opposite the first side. The first and second rails 60, 62 may extend continuously or intermittently along the shaft 54. The first and second rails 60, 62 may have a cross-section which complements the cross-section of the first and second slots 30, 32 of the implant guide 10. For example, in some embodiments the first and second rails 60, 62 may have a T-shaped configuration, a trapezoidal configuration, or other desired configuration complementing the configuration of the first and second slots 30, 32. Such a configuration may prevent disengagement of the rails 60, 62 of the docking member 50 from the slots 30, 32 in a lateral direction perpendicular to the longitudinal axis of the first and second rails 60, 62. For instance, the interaction of the rails 60, 62 with the slots 30, 32 may prevent the first and second legs 16, 18 of the implant guide 10 from splaying laterally outward during a medical procedure.

The docking member 50, or portions thereof, may be formed of any desired material including, but not limited to, those polymeric and metallic materials discussed above regarding the implant guide 10. In some embodiments, the docking member 50, when inserted along the shaft 14 of the implant guide 10, may inhibit the ability of the shaft 14 to flexibly bend and/or may help retain the shaft 14 in a desired configuration as desired.

Figure 3:
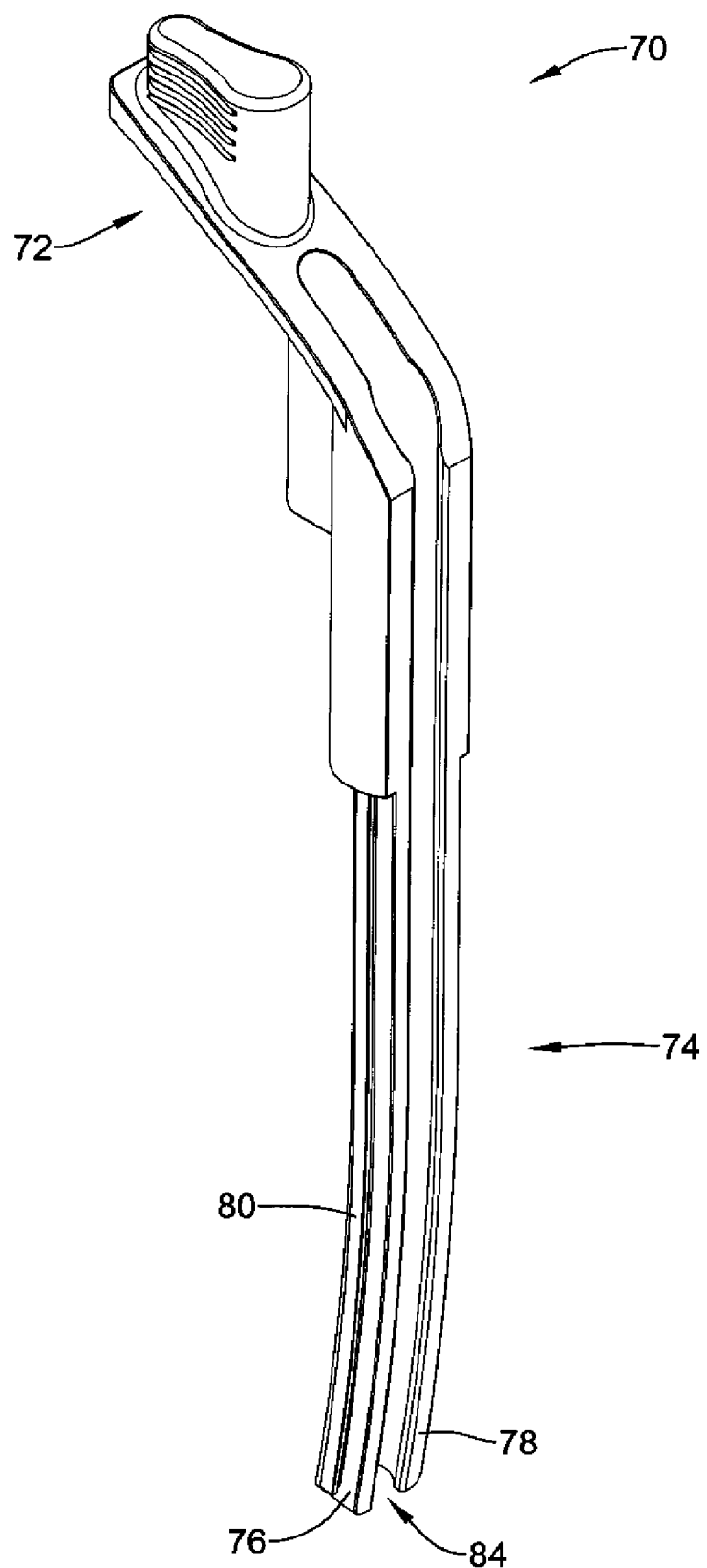
FIG. 3 is a perspective view of an illustrative stabilization insert for use with the implant guide of FIG. 1.
Figure 3A:
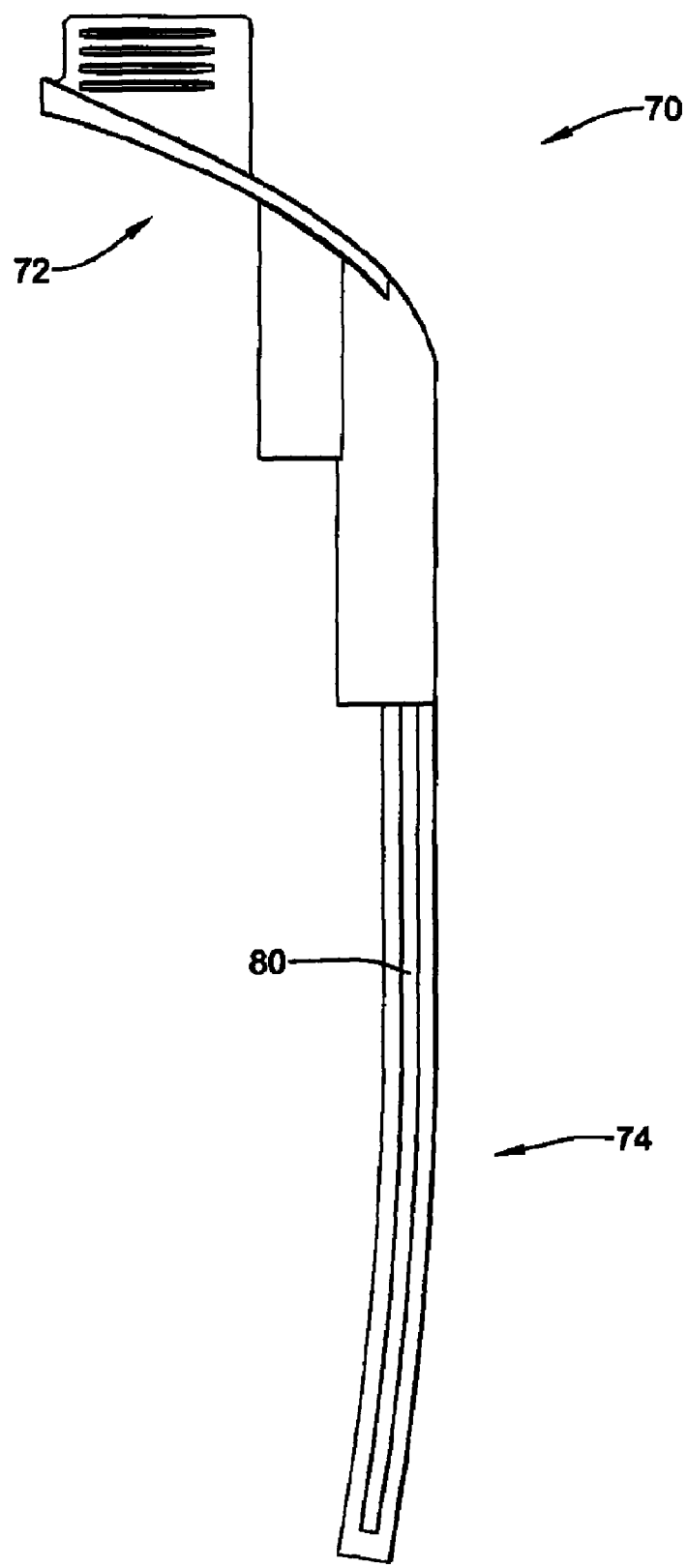
FIG. 3A is a side view of the stabilization insert of FIG. 3.
Figure 3B:
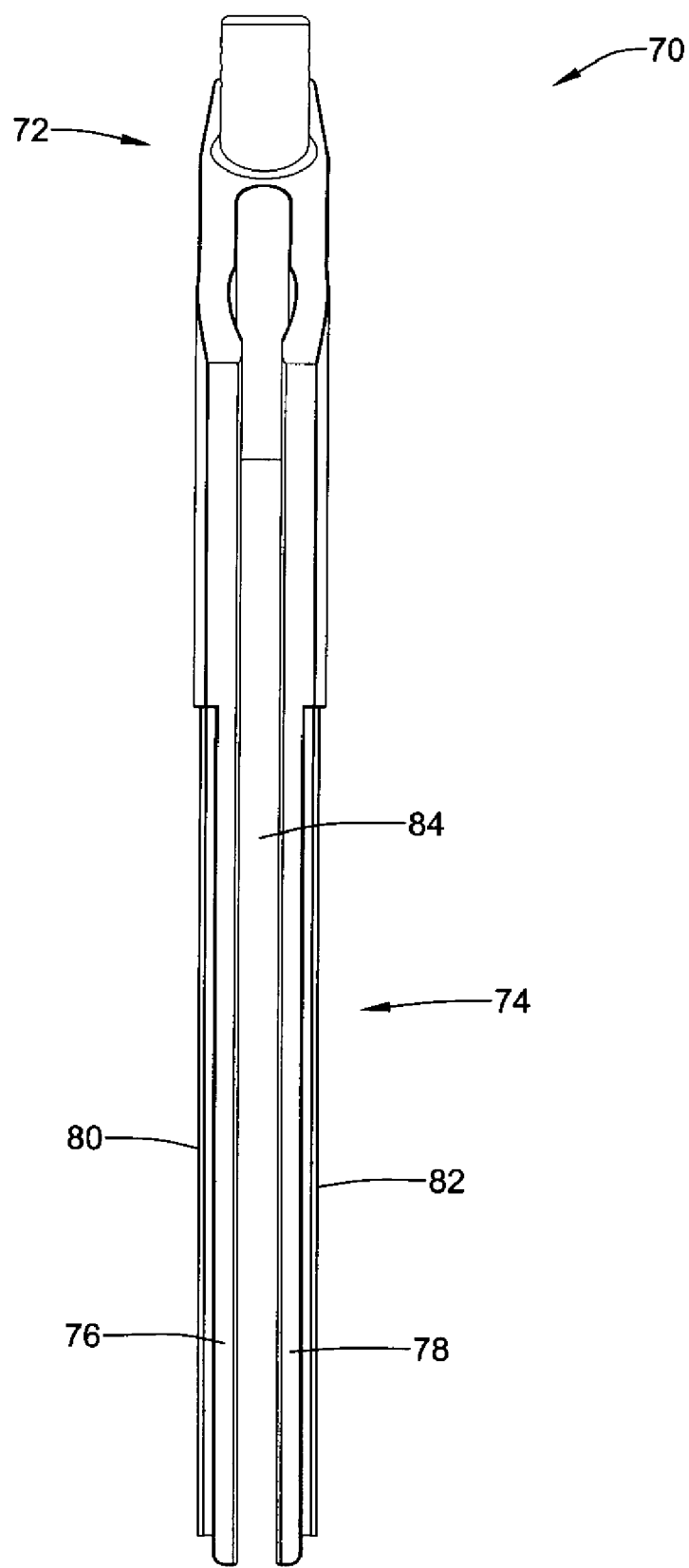
FIG. 3B is a front view of the stabilization insert of FIG. 3.

Another insert, in the form of a stabilizing insert 70 which may be used in association with the implant guide 10 of FIG. 1 is illustrated in FIGS. 3, 3A and 3B. The stabilizing insert 70 may include a handle 72 and a shaft 74 extending distally from the handle 72. In some embodiments, the shaft 74 may include a first leg 76 and a second leg 78. The first leg 76 may be spaced from the second leg 78, providing a channel 84 between the first leg 76 and the second leg 78. The channel 84 may extend from a proximal portion of the shaft 74 to the distal end of the shaft 74, separating the first leg 76 and the second leg 78 at the distal end of the shaft 74.

The shaft 74 of the stabilizing insert 70 may include one or more engagement features which may interact with one or more complementary engagement features of the shaft 14 of the implant guide 10. For instance, the shaft 74 of the stabilizing insert 70 may include an engagement feature which interacts with an engagement feature of the first leg 16 of the implant guide 10 and an engagement feature which interacts with an engagement feature of the second leg 18 of the implant guide 10. The interaction of the complementary engagement features of the implant guide 10 and the stabilizing insert 70 may allow relative movement between the stabilizing insert 70 and the implant guide 10. For instance, the complementary engagement features may allow sliding movement of the stabilizing insert 70 relative to the implant guide 10.

For instance, the shaft 74 of the stabilizing insert 70 may include a first rail 80 extending along a first side of the shaft 74 and/or a second rail 82 extending along a second side of the shaft 74 opposite the first side. The first and second rails 80, 82 may extend continuously or intermittently along the shaft 74. The first and second rails 80, 82 may have a cross-section which complements the cross-section of the first and second slots 30, 32 of the implant guide 10. For example, in some embodiments the first and second rails 80, 82 may have a T-shaped configuration, a trapezoidal configuration, or other desired configuration complementing the configuration of the first and second slots 30, 32. Such a configuration may prevent disengagement of the rails 80, 82 of the stabilizing insert 70 from the slots 30, 32 in a lateral direction perpendicular to the longitudinal axis of the first and second rails 80, 82. For instance, the interaction of the rails 80, 82 with the slots 30, 32 may prevent the first and second legs 16, 18 of the implant guide 10 from splaying laterally outward during a medical procedure.

In some embodiments, the shaft 74 of the stabilizing insert 70 may be a curved shaft having a desired curvature, while in other embodiments the shaft 74 of the stabilizing insert 70 may be straight. In some circumstances, it may be desirable to provide an operator with a collection of stabilizing inserts 70 of different configurations. For instance the collection could include a stabilizing insert 70 with a straight shaft 74 and/or one or more, or a plurality of stabilizing inserts 70 with curved shafts 74 of various degrees of curvature.

The stabilizing insert 70, or portions thereof, may be formed of any desired material including, but not limited to, those polymeric and metallic materials discussed above regarding the implant guide 10. In some embodiments, the stabilizing insert 70, when inserted along the shaft 14 of the implant guide 10, may inhibit the ability of the shaft 14 to flexibly bend and/or may help retain the shaft 14 in a desired configuration as desired.

Figure 4:
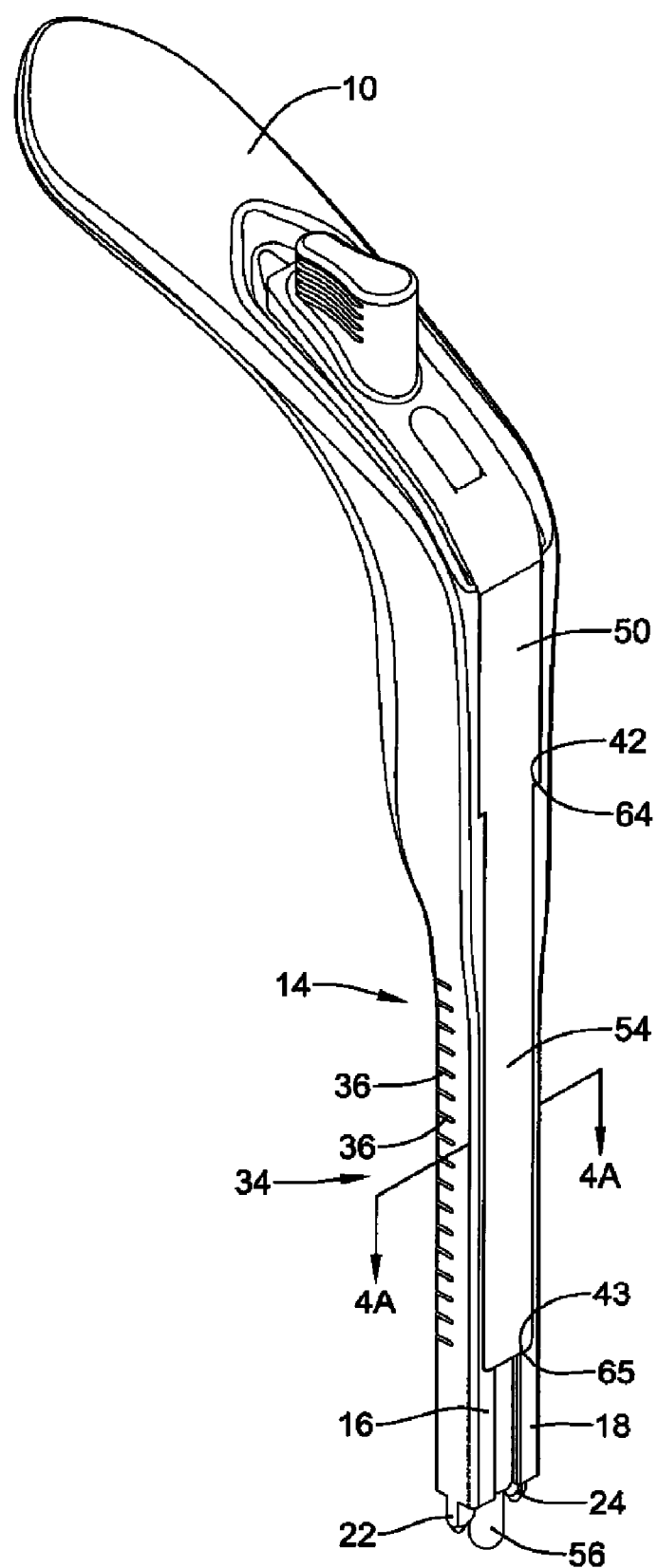
FIG. 4 is a perspective view of an assembly including the guide of FIG. 1 with the docking member of FIG. 2 positioned therewith.

FIG. 4 illustrates the docking member 50 inserted along the shaft 14 of the implant guide 10. As shown in FIG. 4, the shaft 54 of the docking member 50 may be positioned in the channel 20 between the first leg 16 and the second leg 18 of the shaft 14 of the implant guide 10. In some embodiments, the shaft 54 of the docking member 50 may be slidably disposed in the channel 20 such that the shaft 54 of the docking member 50 may slide proximally and distally relative to the shaft 14 of the implant guide 10. The docking member 50 may be slidably positioned along the shaft 14 such that at least a distal portion of the post 56 extends distally of the distalmost portion of the implant guide 10, such as the distal ends of the first and second tangs 22, 24. In some embodiments, a surface 64, 65 of the docking member 50 may abut or otherwise contact a surface 42, 43 of the implant guide 10 when the docking member 50 is fully advanced along the shaft 14. The interaction of the surface 64 and/or 65 of the docking member 50 and the surface 42 and/or 43 of the implant guide 10 may act as a stop to prevent further distal advancement of the docking member 50 relative to the implant guide 10.

Figure 4A:
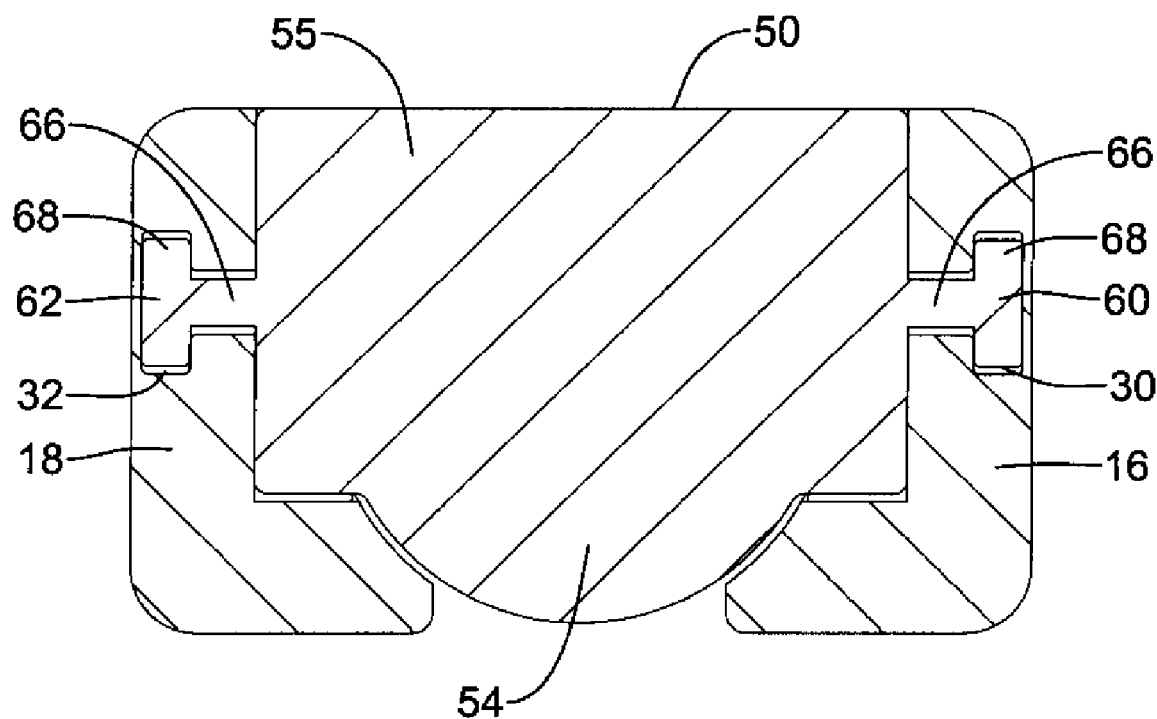
FIG. 4A is a cross-section taken of the assembly of FIG. 4 along line 4-4.

FIG. 4A is a cross-sectional view taken across the shaft 14 of the implant guide 10 with the shaft 54 of the docking member 50 inserted therewith. As shown in FIG. 4A, the first and second rails 60, 62 of the docking member 50 may be positioned in the first and second slots 30, 32, respectively, when the docking member 50 is inserted with the implant guide 10. In the illustrated embodiment, the rails 60, 62 have a T-shape in which a narrower portion 66 of the rails 60, 62 are positioned between a wider portion 68 of the rails 60, 62 and the main body portion 55 of the shaft 54. It is noted that in other embodiments the rails 60, 62 may have a different configuration. For instance, in some embodiments the rails 60, 62 may have a trapezoidal shape, an L-shape, or other shape in which a narrower portion of the rails 60, 62 are positioned between a wider portion of the rails 60, 62 and the main body portion 55 of the shaft 54. The slots 30, 32 may be shaped so as to have a complementary geometry as the rails 60, 62. In such embodiments, the first and second rails 60, 62 may engage with and/or interlock with the first and second slots 30, 32. It is noted that in some embodiments, the rails 60, 62 may be reversed with the slots 30, 32 such that the implant guide 10 includes the rails 60, 62 and the docking member 50 includes the slots 30, 32.

Figure 5:
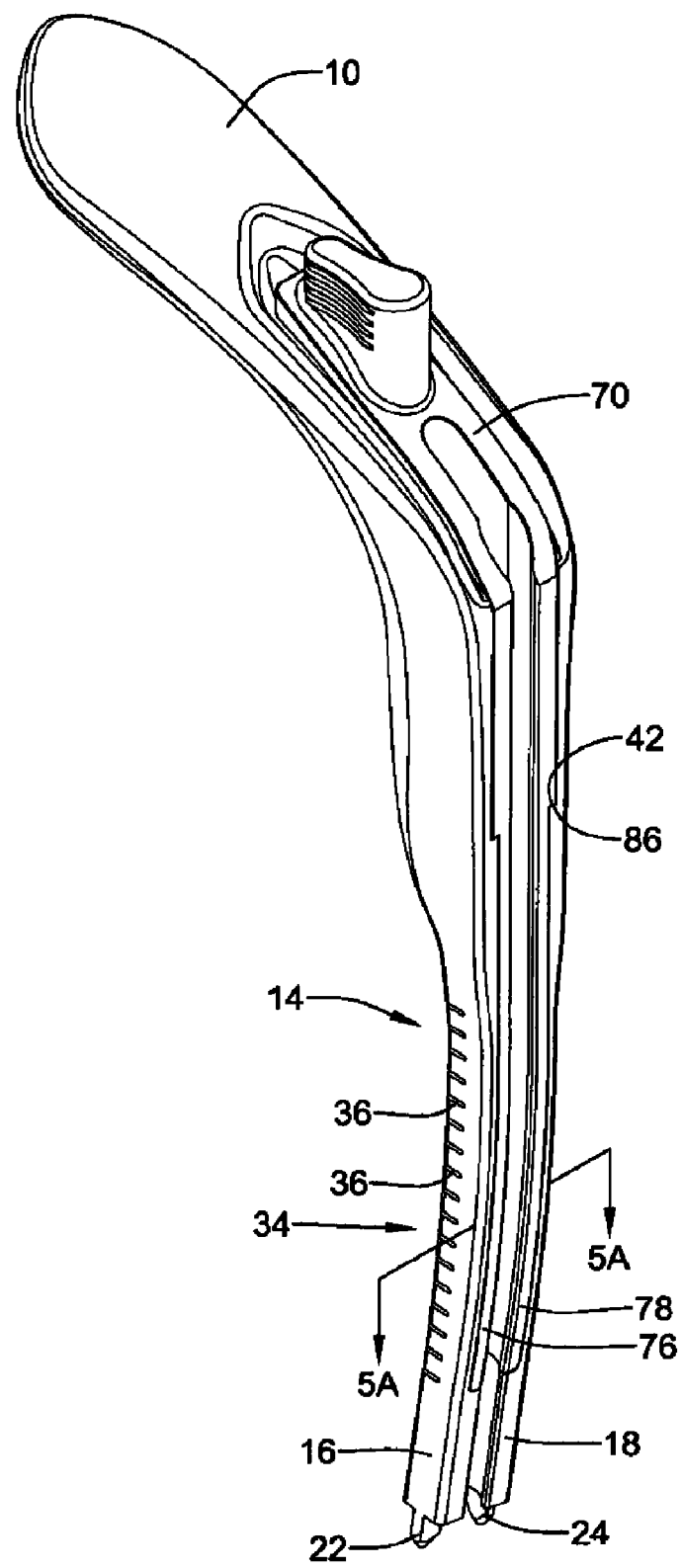
FIG. 5 is a perspective view of an assembly including the guide of FIG. 1 with the stabilization insert of FIG. 3 positioned therewith.

FIG. 5 illustrates the stabilizing insert 70 inserted along the shaft 14 of the implant guide 10. As shown in FIG. 5, the shaft 74 of the stabilizing insert 70 may be positioned in the channel 20 between the first leg 16 and the second leg 18 of the shaft 14 of the implant guide 10. In some embodiments, the shaft 74 of the stabilizing insert 70 may be slidably disposed in the channel 20 such that the shaft 74 of the stabilizing insert 70 may slide proximally and distally relative to the shaft 14 of the implant guide 10. In some embodiments, a surface 86 of the stabilizing insert 70 may abut or otherwise contact a surface 42 of the implant guide 10 when the stabilizing insert 70 is fully advanced along the shaft 14. The interaction of the surface 86 of the stabilizing insert 70 and the surface 42 of the implant guide 10 may act as a stop to prevent further distal advancement of the stabilizing insert 70 relative to the implant guide 10.

As can be seen in FIG. 5, the stabilizing insert 70 may impart a curvature to the shaft 14 of the implant guide 10 when inserted along the shaft 14. The curvature imparted on the shaft 14 may be reflective of the curvature of the shaft 74 of the stabilizing inert 70. With the stabilizing insert 70 inserted along the shaft 14, the stabilizing insert 70 may inhibit the shaft 14 of the implant guide 10 from reverting back to a first configuration, such as an equilibrium configuration, after being subjected to a second configuration by the stabilizing insert 70. For instance, the curved shaft 74 of the stabilizing insert 70 may place the shaft 14 of the implant guide 10 into a desired curved configuration, and thus inhibit the shaft 14 from returning to an equilibrium configuration, such as a straight configuration. In some embodiments, the equilibrium configuration of the shaft 14 may be a curved configuration, thus the stabilizing insert 70 may reshape the shaft 14 to a second configuration such as a straight configuration or a different curved configuration. In embodiments in which the shaft 74 of the stabilizing insert 70 is straight, the stabilizing insert 70 may hold the shaft 14 of the implant guide 10 in a straight configuration, inhibiting the shaft 14 from being bent away from a longitudinal axis of the shaft 14.

Figure 5A:
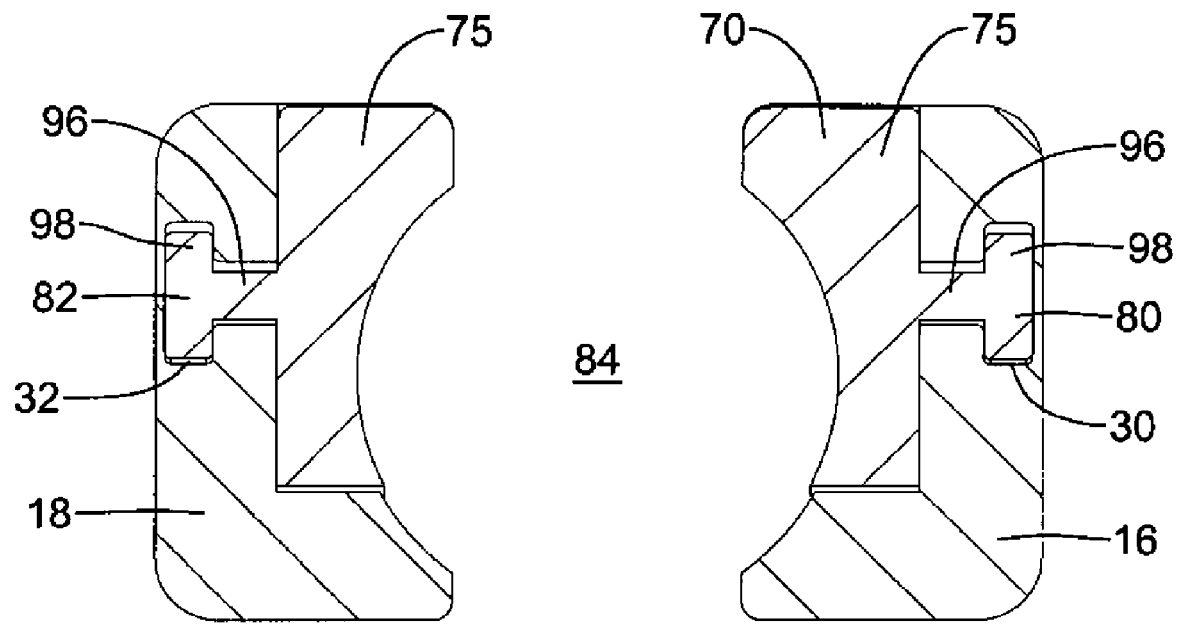
FIG. 5A is a cross-section taken of the assembly of FIG. 5 along line 5-5.

FIG. 5A is a cross-sectional view taken across the shaft 14 of the implant guide 10 with the shaft 74 of the stabilizing insert 70 inserted therewith. As shown in FIG. 5A, the first and second rails 80, 82 of the stabilizing insert 70 may be positioned in the first and second slots 30, 32, respectively, when the stabilizing insert 70 is inserted with the implant guide 10. In the illustrated embodiment, the rails 80, 82 have a T-shape in which a narrower portion 96 of the rails 80, 82 are positioned between a wider portion 98 of the rails 80, 82 and the main body portion 75 of the shaft 74. It is noted that in other embodiments the rails 80, 82 may have a different configuration. For instance, in some embodiments the rails 80, 82 may have a trapezoidal shape, an L-shape, or other shape in which a narrower portion of the rails 80, 82 are positioned between a wider portion of the rails 80, 82 and the main body portion 75 of the shaft 74. The slots 30, 32 may be shaped so as to have a complementary geometry as the rails 80, 82. In such embodiments, the first and second rails 80, 82 may engage with and/or interlock with the first and second slots 30, 32. It is noted that in some embodiments, the rails 80, 82 may be reversed with the slots 30, 32 such that the implant guide 10 includes the rails 80, 82 and the stabilizing insert 70 includes the slots 30, 32.

FIGS. 6A-6E illustrate a method of using the implant guide 10 during an installation procedure with the docking member 50 and the stabilizing insert 70. During a medical procedure, a vertebral anchor 100 may be secured to a bone of a spinal column. In some embodiments, the vertebral anchor 100 may be a pedicle screw, such as a polyaxial or monoaxial pedicle screw, screwed into or otherwise anchored to a pedicle region or other region of a vertebra 2. The vertebral anchor 100 may include a head portion 102 and a shaft portion 104 extending from the head portion 102. The shaft portion 104 may include helical threads 106 for screwing the vertebral anchor 100 into a bone.

The vertebral anchor 100 may be a top-loading pedicle screw in which the head portion 102 includes a saddle 120 configured to receive an elongate member. For example, the saddle 120 may include a first arm 116 and a second arm 118 extending from a base portion 122 of the saddle 120. The first arm 116 may be spaced away from the second arm 118, defining a channel 128, such as a U-shaped channel, extending through the head portion 102 from a first side surface 124 to a second side surface 126 of the head portion 102.

The head portion 102 may include an opening 108, such as a threaded opening, extending into the channel 128 from an upper surface 110 of the head portion. In some embodiments, the opening 108 may have a central axis which is co-axial with the shaft 104 of the vertebral anchor 100. The threaded opening 108 may be configured to threadedly receive a threaded fastener (not shown), such as a set screw to secure an elongate member in the channel 128 of the head portion 102.

The head portion 102 may also be configured to engage with the distal end 26 of the insert guide 10. For instance, the head portion 102 may include a first notch 112 and a second notch 114 shaped and sized to receive the first tang 22 and the second tang 24, respectively, of the implant guide 10. The first notch 112 may be located in the first arm 116 of the saddle 120. The first notch 112 may extend from the upper surface 110 of the head portion 102 toward the shaft 104. The first notch 112 is shown as having a trapezoidal shape with a wider portion of the first notch 112 closer to the central longitudinal axis of the vertebral anchor 100 than a narrower portion of the first notch 112. The second notch 114 may be located in the second arm 118 of portion 102 toward the shaft 104. The second notch 114 is shown as having a trapezoidal shape with a wider portion of the second notch 114 closer to the central longitudinal axis of the vertebral anchor 100 than a narrower portion of the second notch 114. The configuration of the first and second notches 112, 114 and/or the tangs 22, 24 of the insert guide 10 may prevent splaying outward of the first and second legs 16, 18 during a medical procedure.

Other examples of possible arrangements for engaging the distal end 26 of the insert guide 10 with the head portion 102 of the vertebral anchor 100 are shown and described in U.S. patent application Ser. Nos. 11/539,287, 11/737,151, 11/743,481, and 12/025,984, the disclosures of which are incorporated herein by reference.

Figure 6A:
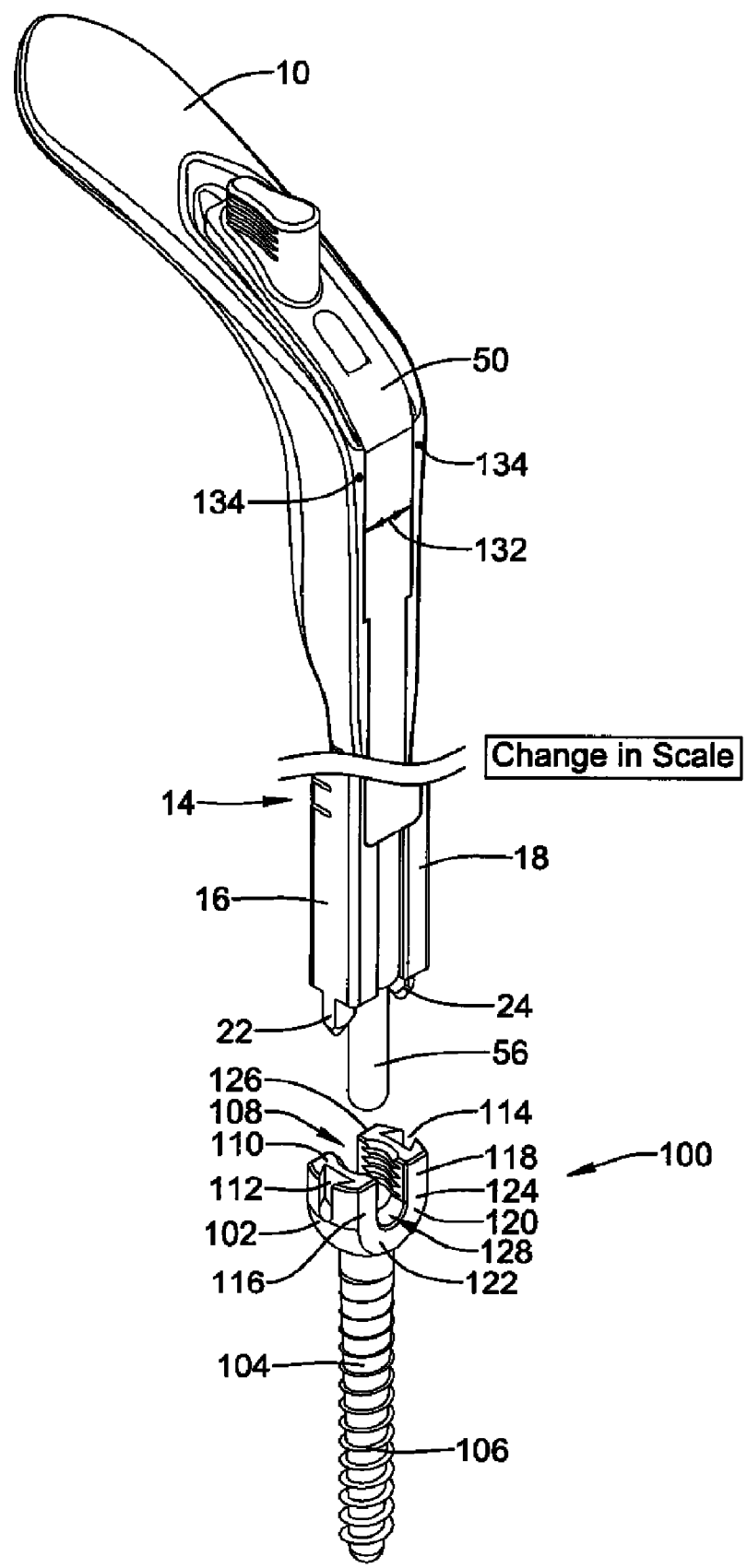
FIGS. 6A-6E illustrate an exemplary method of using the implant guide of FIG. 1 during an installation procedure with the docking member of FIG. 2 and the stabilization insert of FIG. 3.
Figure 6B:
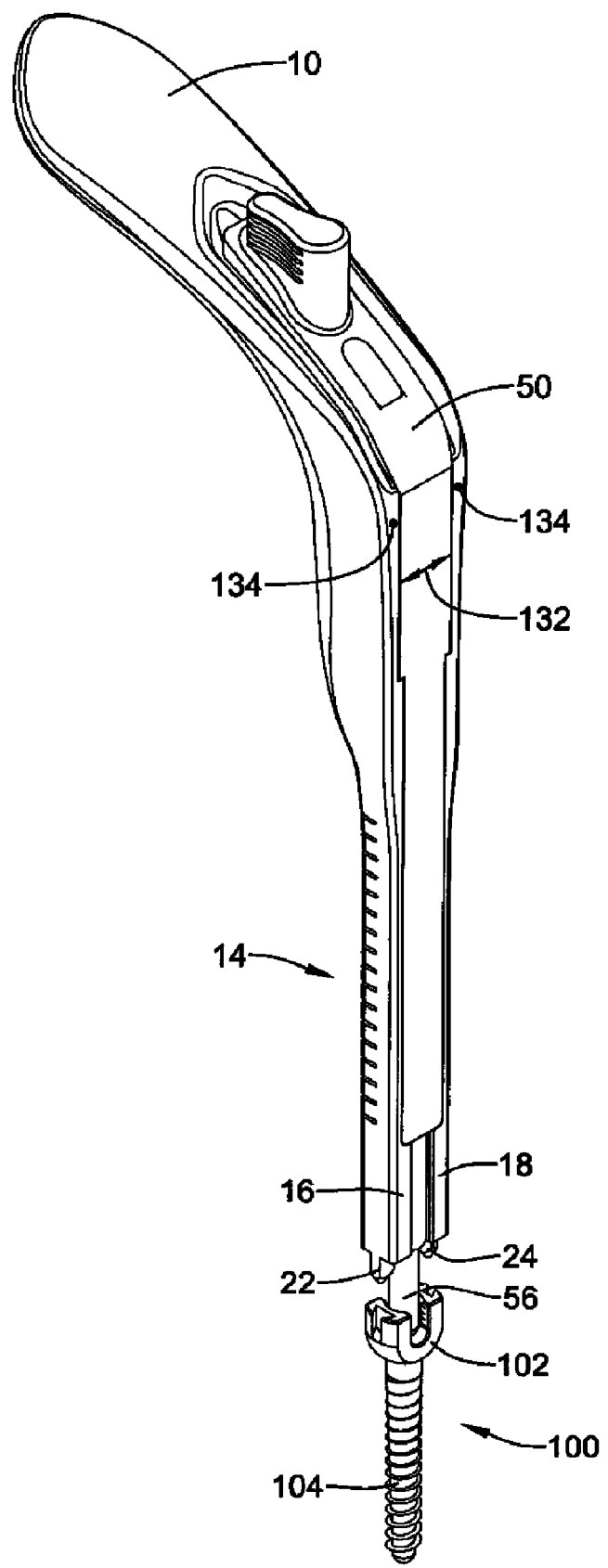

Also shown in FIG. 6A is the distal portion of the installation assembly including the insert guide 10 and the docking member 50 inserted along the shaft 14 of the insert guide 10 prior to docking the insert guide 10 with the vertebral anchor 100. While advancing the insert guide 10 and the docking member 50 to the vertebral anchor 100, the docking member 50 may be advanced to its distalmost extent relative to the insert guide 10 such that at least a distal portion of the post 56 extends distally of the first and second tangs 22, 24 of the insert guide 10. As shown in FIG. 6A, the first and second tangs 22, 24 of the insert guide 10 may have a trapezoidal shape complementing the trapezoidal shape of the first and second notches 112, 114 of the head portion of the vertebral anchor 100.

During a procedure in which the insert guide 10 is docked or engaged with the head portion 102 of the vertebral anchor 100, the combination of the insert guide 10 and the docking member 50 may be advanced distally toward the vertebral anchor 100. The post 56 of the docking member 50 may be first inserted into the threaded opening 108 of the head portion 102 of the vertebral anchor 100, shown in FIG. 6B. With the post 56 fully inserted into the threaded opening 108, the insert guide 10 may remain disengaged from the vertebral anchor 100. In other words, with the post 56 fully inserted into the threaded opening 108, the tangs 22, 24 of the insert guide 10 may remain spaced away from the notches 112, 114 of the head portion 102 of the vertebral anchor 100.

With the post 56 of the docking member 50 inserted into the threaded opening 108, the insert guide 10 may be slid or translated distally relative to the docking member 50 toward the head portion 102 of the vertebral anchor 100. As the implant guide 10 is moved distally relative to the docking member 50, the first and second tangs 22, 24 may enter the first and second notches 112, 114, respectfully. The docking member 50, with its first and second rails 60, 62 slidably engaged in the first and second slots 30, 32 of the implant guide 10, may prevent the first and second legs 16, 18 of the implant guide 10 from splaying outward, thus ensuring alignment of the first and second tangs 22, 24 with the first and second notches 112, 114, respectively.

The docking member 50 and the implant guide 10 may include visual indicia that may be used to verify that the implant guide 10 is fully engaged with the vertebral anchor 100. For instance, the docking member 50 may include a marking 132, such as a groove, notch, line, dot, or other visual indicia. Additionally, the implant guide 10 may include a marking 134, such as a groove, notch, line, dot, or other visual indicia. The marking 132 on the docking member 50 and the marking 134 on the implant guide 10 may remain exterior of the patient and visible to the medical personnel during the medical procedure. The medical personnel may confirm that the implant guide 10 is fully engaged with the vertebral anchor 100 by visually inspecting when the marking 134 on the implant guide 10 is aligned with the marking 132 on the docking member 50 as shown in FIG. 6C, or otherwise positioned in a predetermined relationship.

In some embodiments, there may be an audible and/or mechanical indication used to verify that the implant guide 10 is fully engaged with the vertebral anchor 100. For instance, the docking member 50 may include a detent interacting with a component of the implant guide 10, or vise versa. Some embodiments may include a ball detent in which a spherical ball interacts and engages in a recess to provide a mechanical indication of when the implant guide 10 is fully engaged with the vertebral anchor 100. Other types of detent arrangements are also contemplated. In some embodiments, the medical personnel may hear a click or other sound to provide verification. In some embodiments, the implant guide 10 and/or the docking member 50 may include other interlocking and/or engagement means providing an audible and/or mechanical indication to verify that the implant guide 10 is fully engaged with the vertebral anchor 100.

Figure 6C:
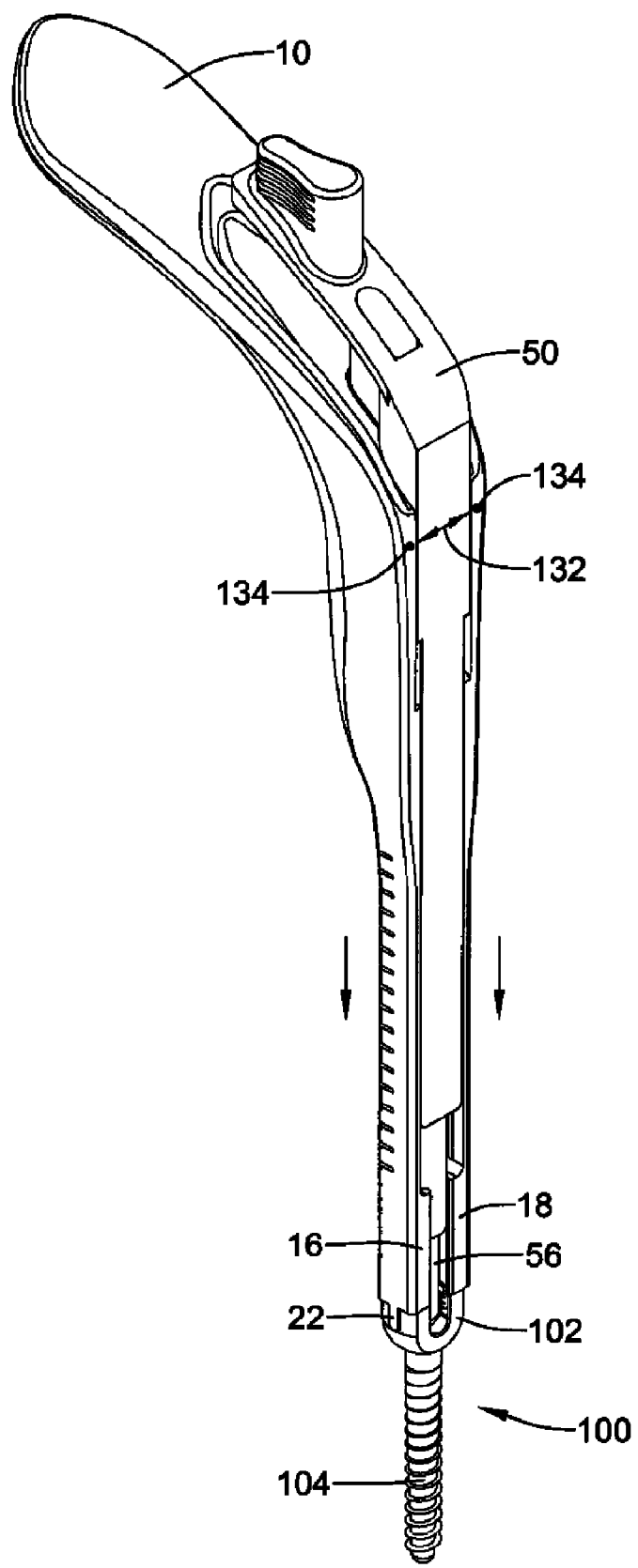
Figure 6D:
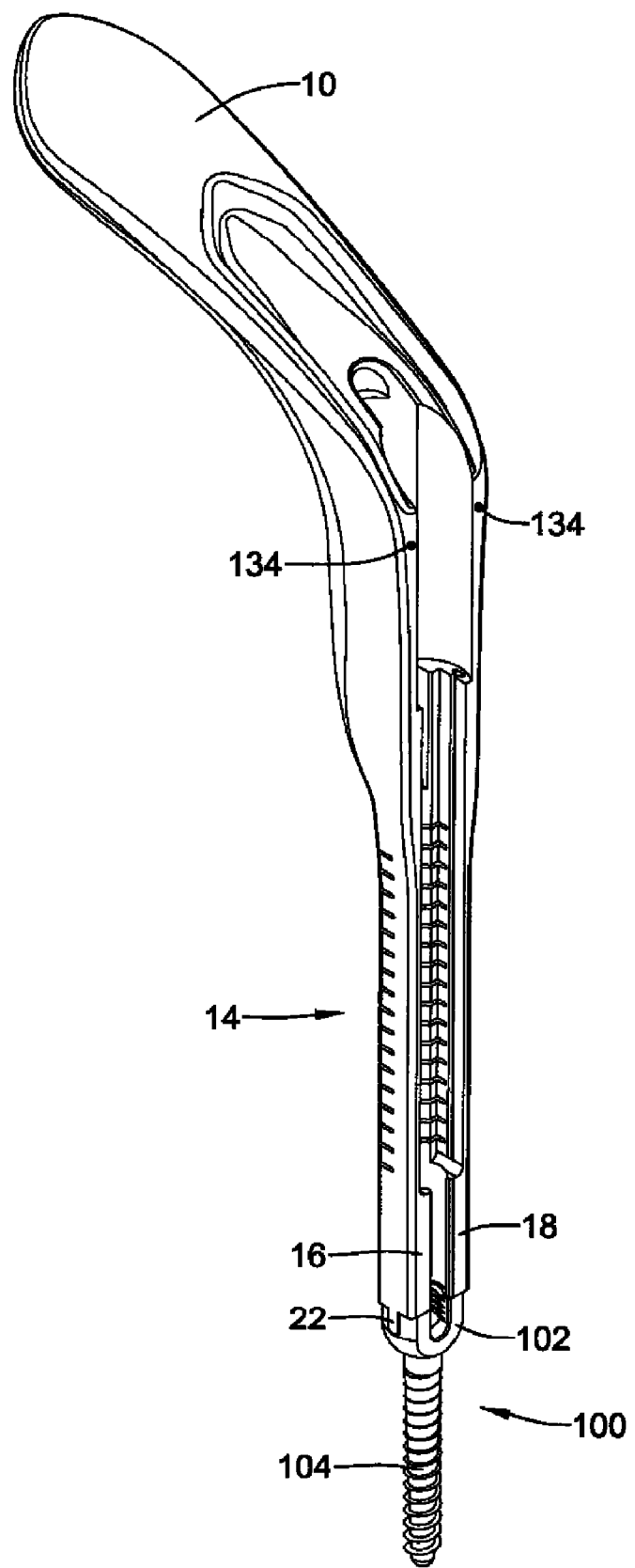

Once the implant guide 10 is fully engaged with the vertebral anchor 100, the implant guide 10 may be held stationary while the docking member 50 is withdrawn proximally from the implant guide 10, leaving the implant guide 10 docked with the vertebral anchor 100, shown in FIG. 6C. With the docking member 50 removed from the implant guide 10, the implant guide 10 may be manipulated to perform one or more functions during the medical procedure. For instance, a force may be applied to the implant guide 10 to distract vertebrae and/or the implant guide 10 may be used to guide one or more components of a vertebral stabilization system toward the spinal column and into engagement with the vertebral anchor 100.

Figure 6E:
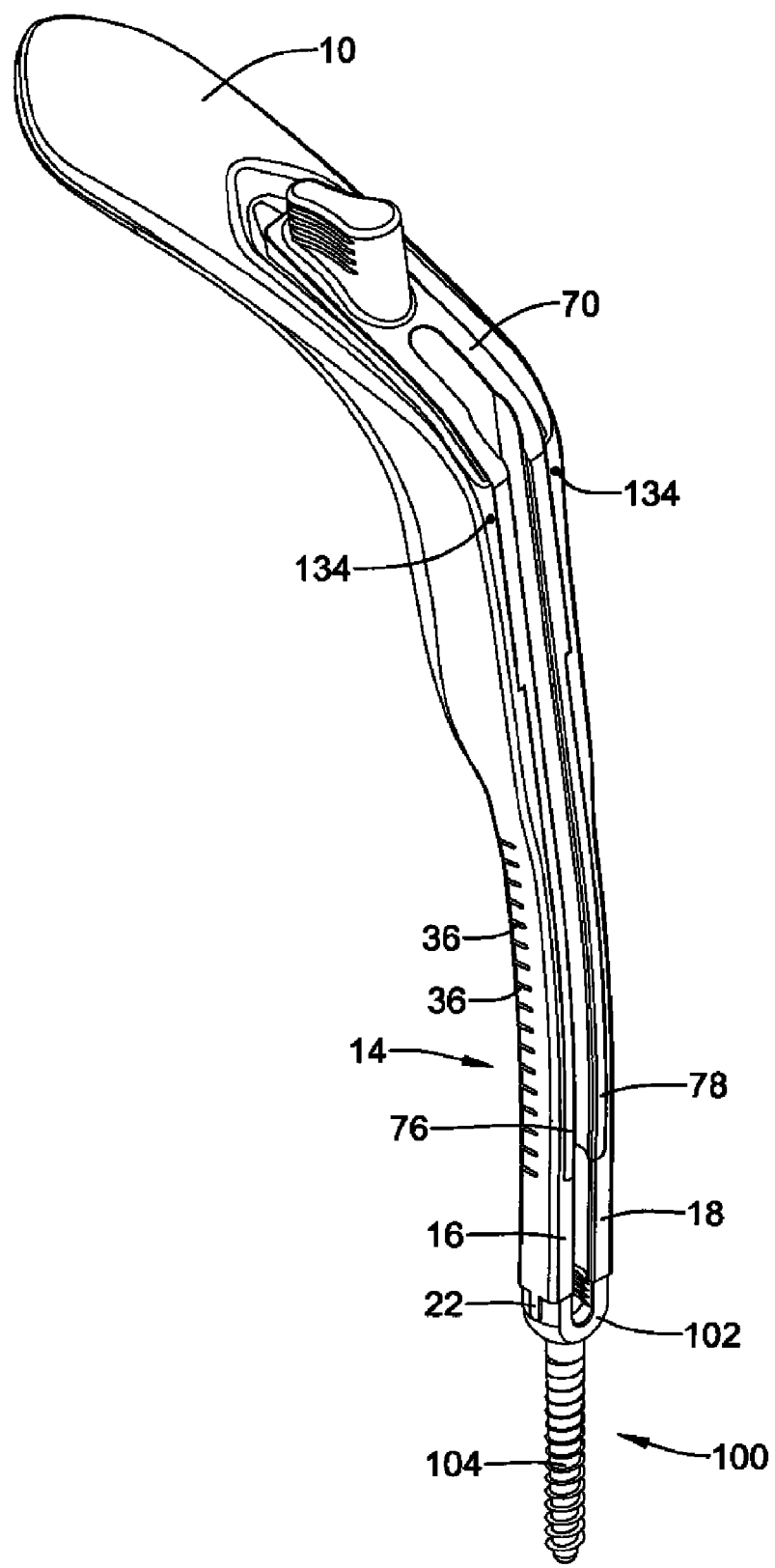

In some circumstances, it may be desirable to inhibit the shaft 14 of the implant guide 10 from flexibly bending, and/or it may be desirable to instill a desired curvature to the shaft 14 of the implant guide 10. As shown in FIG. 6E, with the implant guide 10 docked with the vertebral anchor 100, a stabilization insert 70 may be inserted along the shaft 14 of the implant guide 10. The stabilization insert 70 may inhibit flexing of the shaft 14 of the implant guide 10 and/or may subject the shaft 14 of the implant guide 10 to a desired curvature, consequential of the curvature of the shaft 74 of the stabilization insert 70.

It may be noted that one stabilization insert 70 may be exchanged for another stabilization insert 70 without undocking the implant guide 10 from the vertebral anchor 100. Thus, the shaft 14 of the implant guide 10 may be subjected to a first curvature consequential of the curvature of the shaft 74 of a first stabilization insert 70, and the shaft 14 of the implant guide 10 may be subsequently subjected to a second curvature consequential of the curvature of the shaft 74 of a second stabilization insert 70. Furthermore, the implant guide 10 may be selectively inhibited from bending by selectively inserting a stabilization insert 70 along the shaft 14 and/or selectively allowed to flexibly bend by withdrawing a stabilization insert 70 from the shaft 14, as desired.

Figure 7:
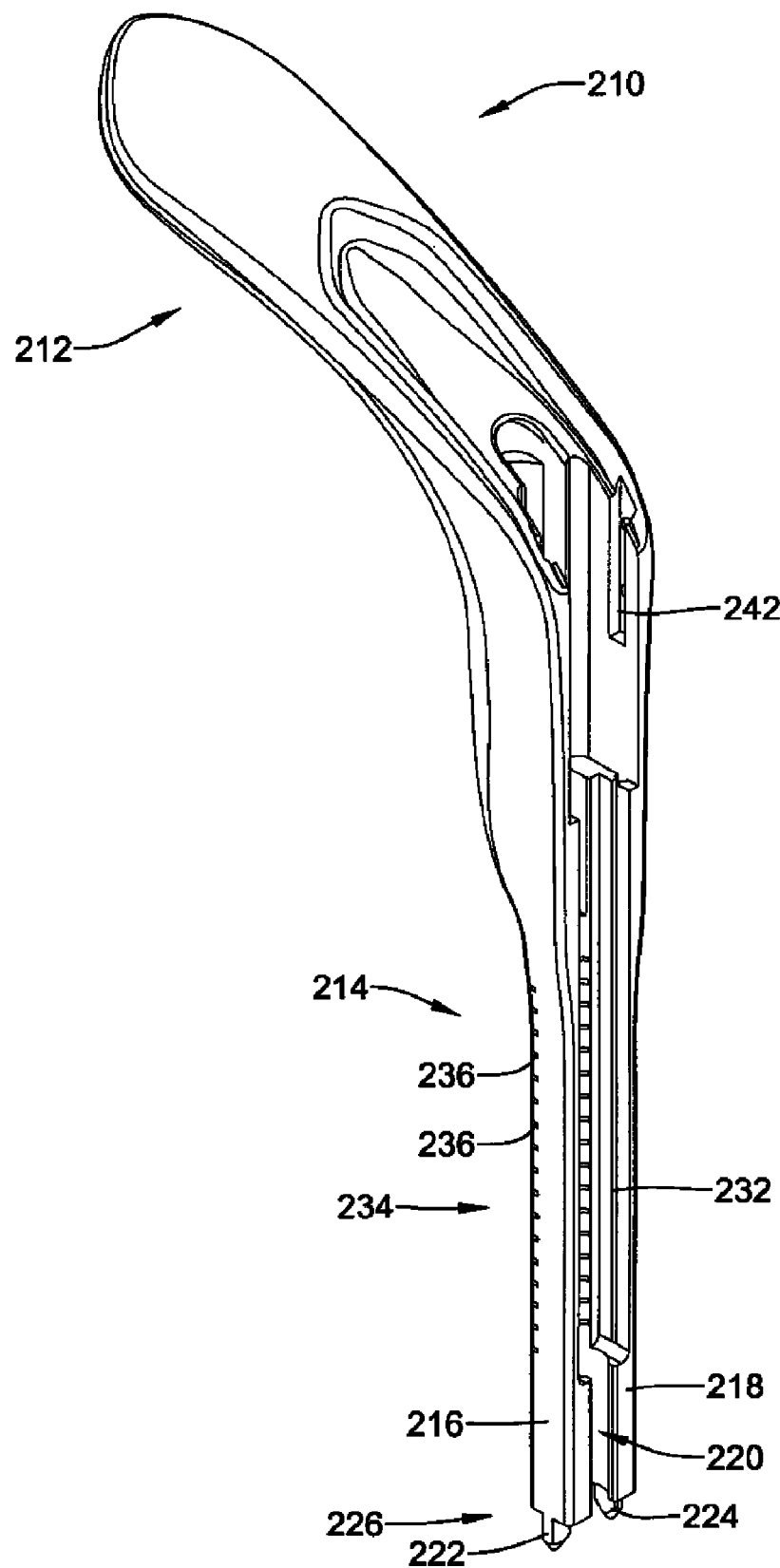
FIG. 7 is a perspective view of an alternative implant guide.

An alternative implant guide 210 is shown in FIG. 7. The implant guide 210 may be similar to the implant guide 10 of FIG. 1 with the exception of some notable differences, some of which are described below. The implant guide 210 may include a handle 212 and a shaft 214 extending distally from the handle 212. The shaft 214 may include a first leg 216 spaced from a second leg 218, defining an elongate channel 220 therebetween. The channel 220 may extend from a proximal portion of the shaft 214 to the distal end 226 of the shaft 214. The implant guide 210 may include a first tang 222 extending distally from the first leg 216 and a second tang 224 extending distally from the second leg 218. The tangs 222, 224 may be configured to engage with a head portion 102 of a vertebral anchor 100. The first leg 216 may also include a first elongate slot 230, and the second leg 218 may include a second elongate slot 232 similar to that described above regarding the implant guide 10. The shaft 214 may include flexibility characteristics 234, such as a plurality of cuts 236, formed along at least a portion of the length of the shaft 214, providing the shaft 214 with a degree of flexibility.

Figure 8:
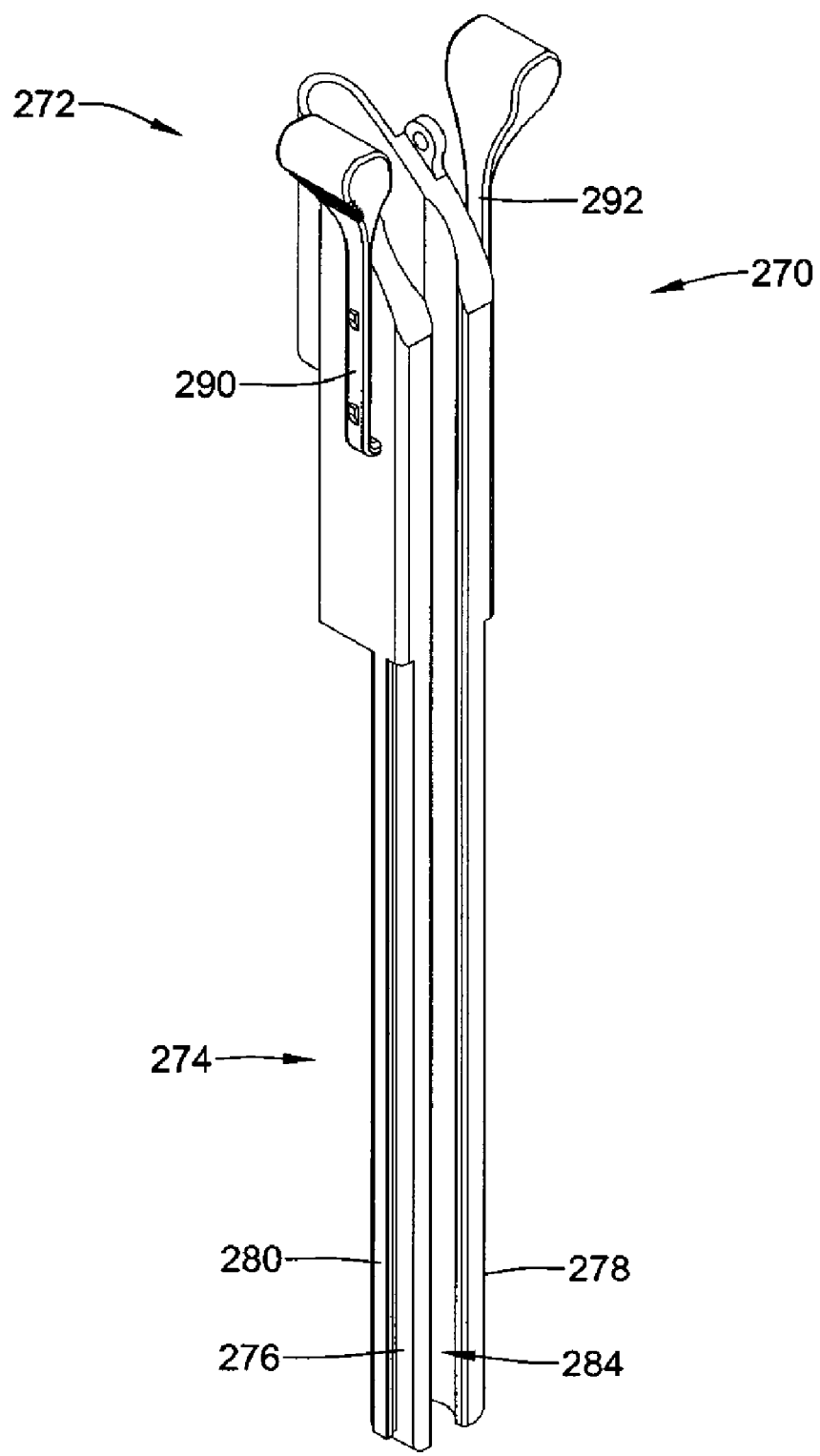
FIG. 8 is a perspective view of an alternative stabilization insert for use with the implant guide of FIG. 7.

An alternative stabilization insert 270 is shown in FIG. 8. The stabilization insert 270 may be similar to the stabilization insert 70 of FIG. 3 with the exception of some notable differences, some of which are described below. The stabilization insert 270 may include a handle 272 and a shaft 274 extending from the handle 272. The shaft 274 may include a first leg 276 spaced from a second leg 278, defining an elongate channel 284 therebetween. The channel 284 may extend from a proximal portion of the shaft 274 to the distal end of the shaft 274. The shaft 274 may include a first rail 280 extending along the first leg 276 and a second rail 282 extending along the second leg 278. The rails 280, 282 may be configured to engage with the slots 230, 232 of the implant guide 210.

Figure 7A:
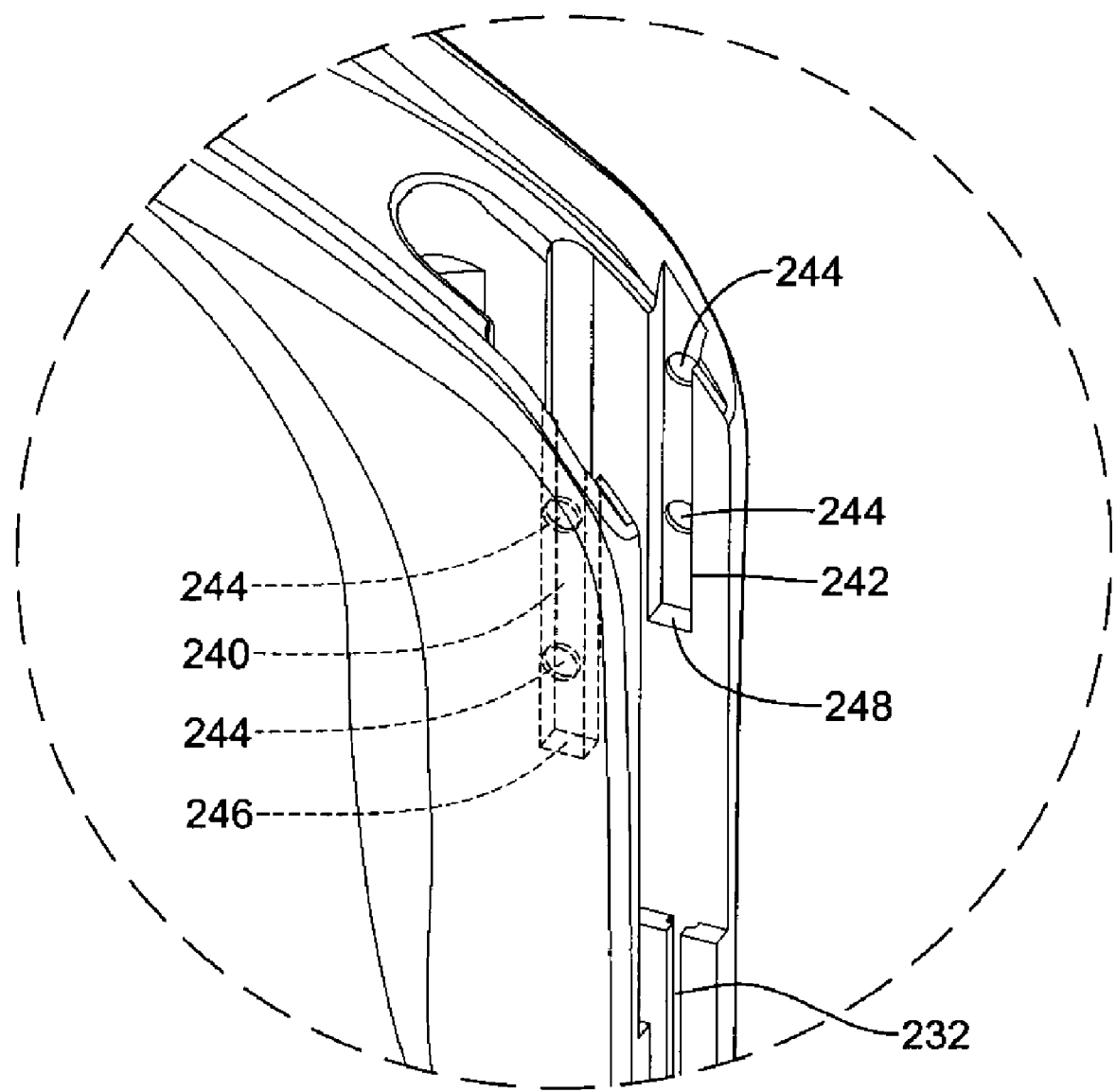
FIG. 7A is an enlarged view of the proximal portion of the implant guide of FIG. 7.
Figure 8A:
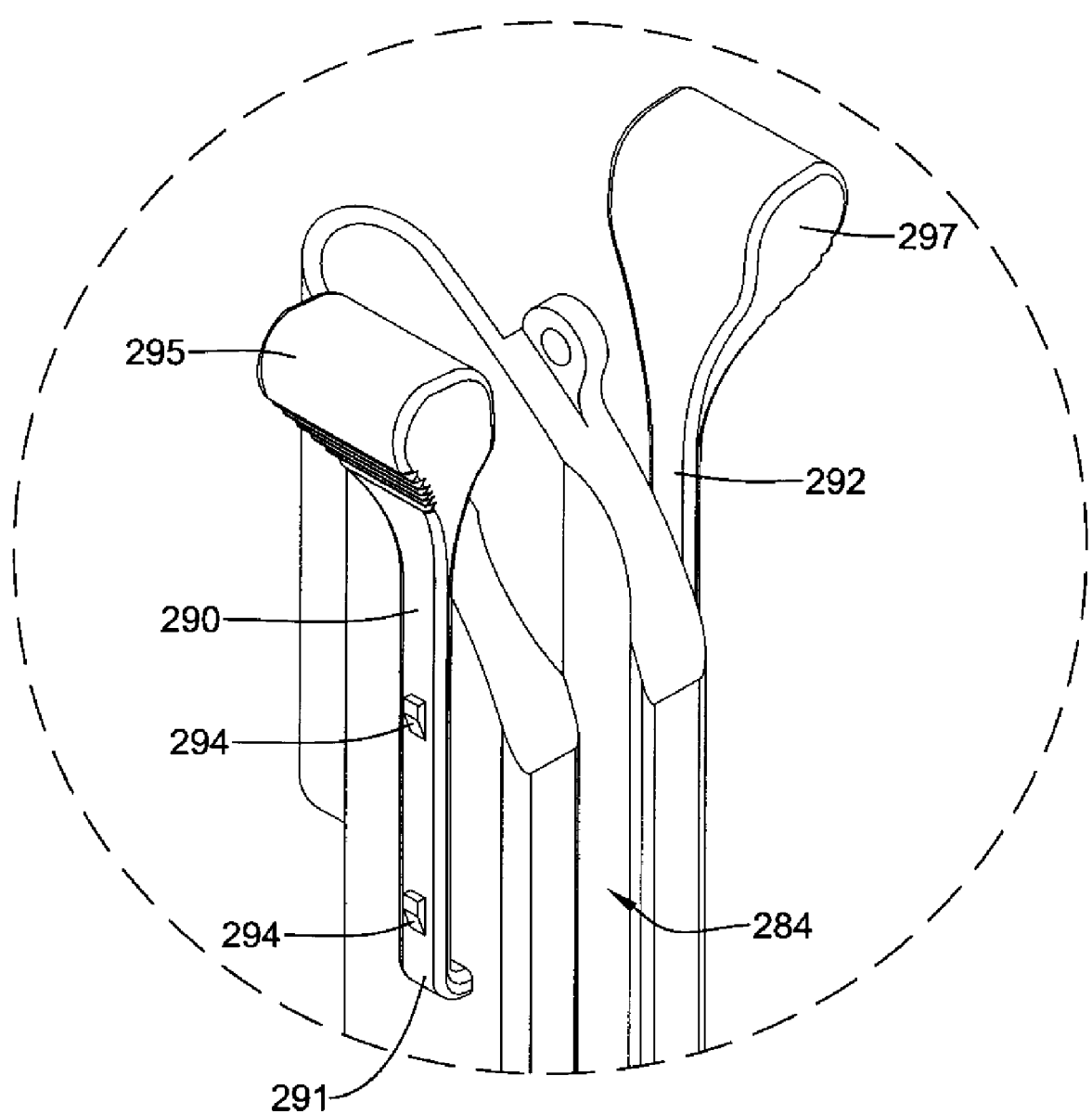
FIG. 8A is an enlarged view of the proximal portion of the stabilization insert of FIG. 8.

The proximal portion of the implant guide 210 may be configured to interlock with a proximal portion of the stabilization insert 270 when the stabilization insert 270 is inserted along the shaft 214 of the implant guide 210. In some embodiments the implant guide 210 may include one or more, or a plurality of interlocking components interacting with one or more, or a plurality of interlocking components of the stabilization insert 270. FIGS. 7A and 8A are enlarged views illustrating an exemplary configuration of the proximal portions of the implant guide 210 and the stabilization insert 270, respectively. FIGS. 9A and 9B, illustrate the interaction of the interlocking components of the implant guide 210 with the interlocking components of the stabilization insert 270 in an engaged and disengaged configuration, respectively.

As shown in FIG. 7A, the proximal portion of the implant guide 210 may include a first channel 240 defined in a wall of the stabilization insert 270 and a second channel 242 defined in a wall of the stabilization insert 270 opposite the first channel 240. The first channel 240 may have an open proximal end and an end surface 246 opposite the open proximal end. The second channel 242 may have an open proximal end and an end surface 248 opposite the open proximal end. The first and second channels 240, 242 may additionally include one or more, or a plurality of indents 244, such as holes or the like.

As shown in FIG. 8A, the proximal portion of the stabilization insert 270 may include a first tongue 290 and a second tongue 292 attached to the shaft 274. A first end 291 of the first tongue 290 may be attached to the shaft 274, while a second end 295 of the first tongue 290 may be spaced from the shaft 274. A first end 293 of the second tongue 292 may be attached to the shaft 274, while a second end 297 of the second tongue 292 may be spaced from the shaft 274. The first and second tongues 290, 292 may be deflected toward one another by pushing the second ends 295, 297 toward one another. The first tongue 290 may be sized and configured to be slidably inserted into the first channel 240 of the implant guide 210 and the second tongue 292 may be sized and configured to be slidably inserted into the second channel 242 of the implant guide 210. The first and second tongues 290, 292 may include one or more, or a plurality of projections 294 configured to mate with the indents 244 of the implant guide 210.

Figure 9:
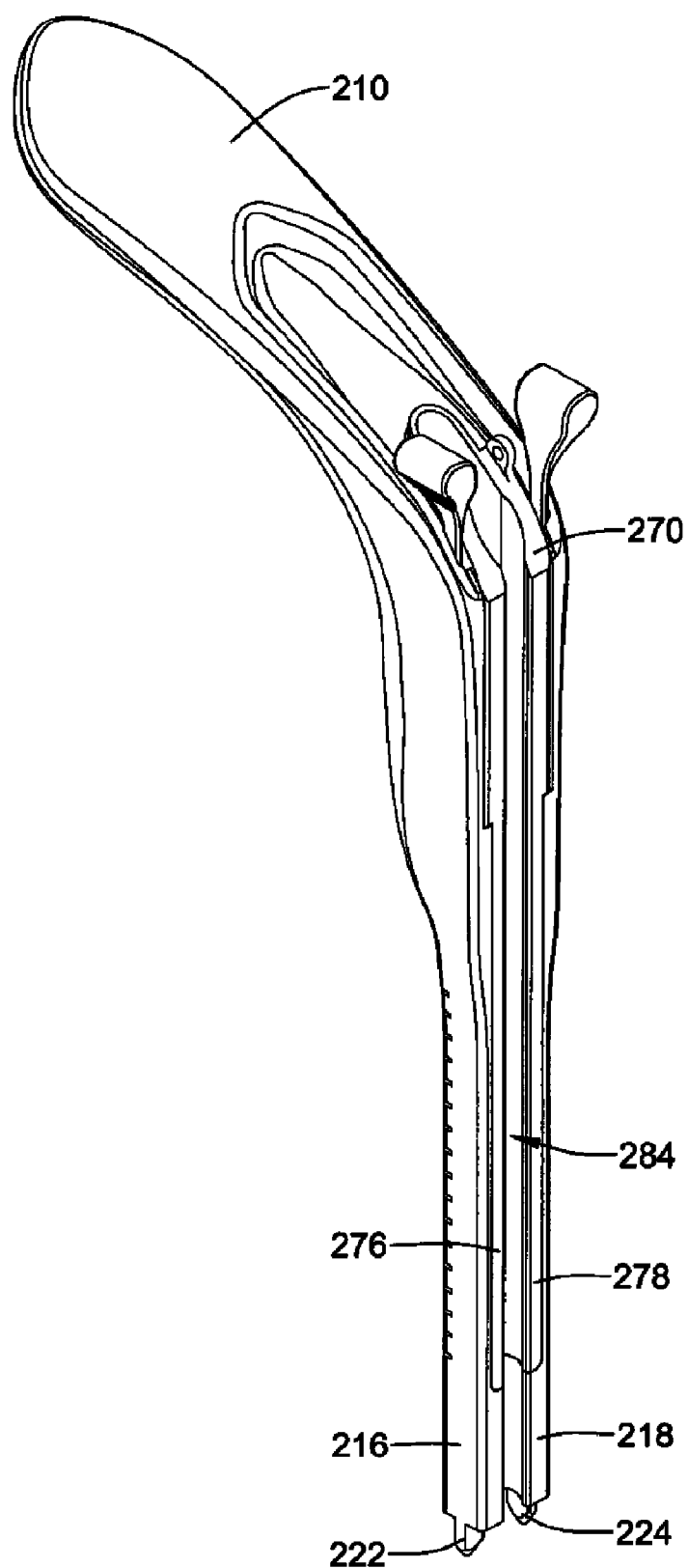
FIG. 9 is a perspective view of the stabilization insert of FIG. 8 inserted with the implant guide of FIG. 7.
Figure 9A:
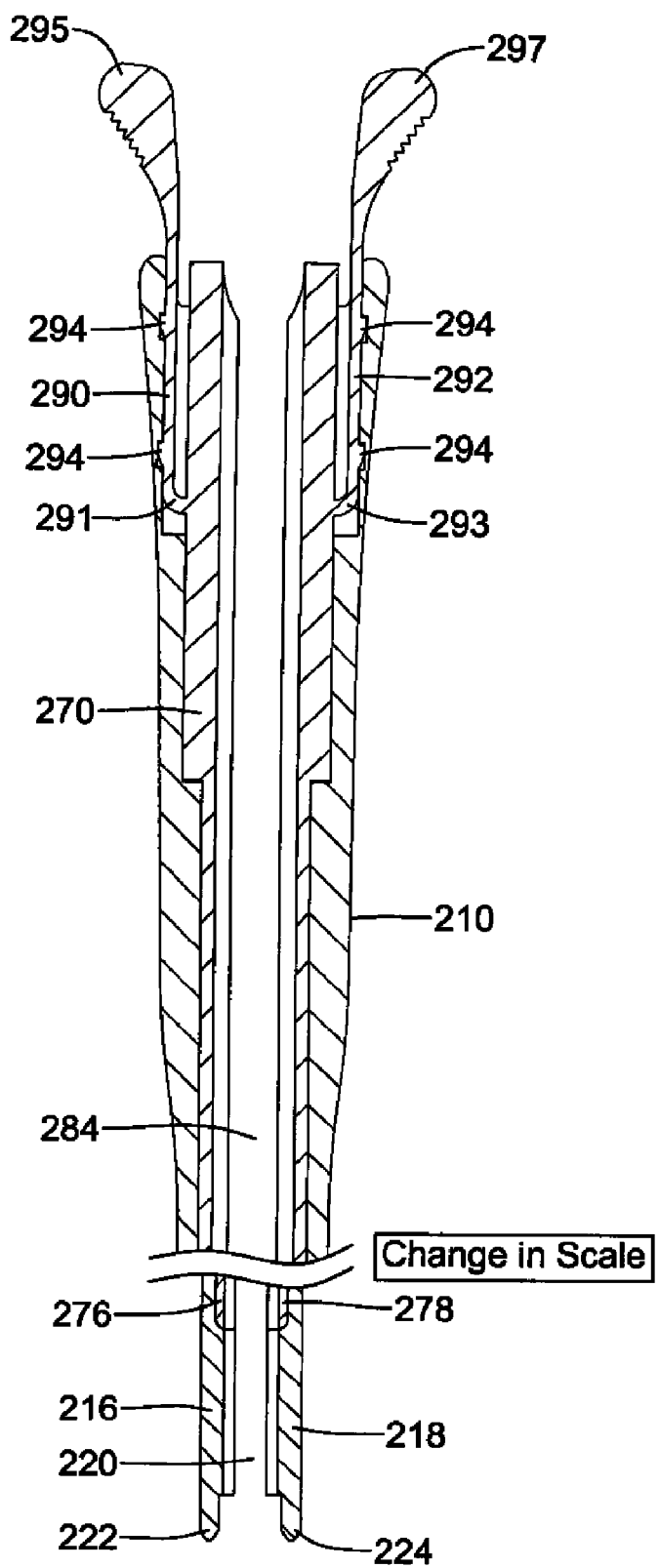
FIGS. 9A and 9B illustrate the engagement of the stabilization insert of FIG. 8 with the implant guide of FIG. 7.
Figure 9B:
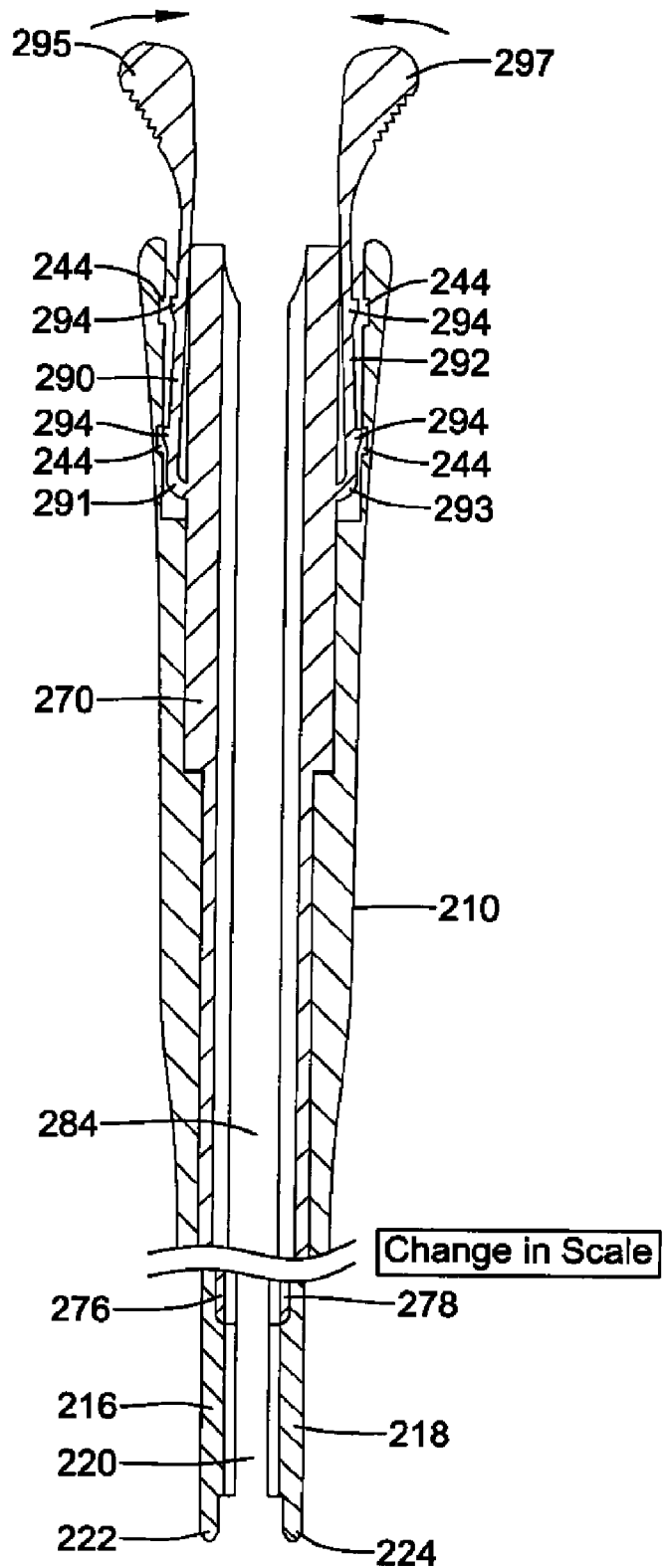

FIG. 9 illustrates the stabilization insert 270 inserted along the shaft 214 of the implant guide 210. FIGS. 9A and 9B illustrate the interaction of the interlocking portion of the implant guide 210 with the interlocking portion of the stabilization insert 270, in an engaged and disengaged configuration, respectively. The shaft 274 of the stabilization insert 270 may be inserted along the shaft 214 of the implant guide 210 between the first leg 216 and the second leg 218 such that the first and second rails 280, 282 of the stabilization insert 270 are slidably disposed in the first and second slots 230, 232 of the implant guide 210. As the stabilization insert 270 is advanced distally relative to the implant guide 210, the first tongue 290 may be advanced into the first channel 240 and the second tongue 292 may be advanced into the second channel 242. In the engaged position shown in FIG. 9A, the projections 294 on the tongues 290, 292 may extend into the indents 244 of the channels 240, 242. Relative movement between the stabilization insert 270 and the implant guide 210 may be restrained when the projections 294 are positioned in the indents 244.

In order to disengage the stabilization insert 270 from the implant guide 210, and thus allow relative movement between the stabilization insert 270 and the implant guide 210, the second ends 295, 297 of the tongues 290, 292 may be urged toward one another, deflecting the tongues 290, 292, By deflecting the tongues 290, 292, the projections 294 are removed from the indents 244, as shown in FIG. 9B. With the projections 294 removed from the indents 244, the stabilization insert 270 may be withdrawn proximally relative to the implant guide 210 in order to remove the stabilization insert 270 from the implant guide 210.

It is noted that although this interlocking configuration with the implant guide 210 has been illustrated in association with the stabilization insert 270, such an interlocking configuration may be used with another type of insert, such as the docking member 50 described above, adapted for use with the implant guide 210.

FIGS. 10A-10D illustrate an exemplary medical procedure of installing a spinal stabilization system with the flexible implant guide 10. Although the illustrated method utilizes the implant guide 10, it is noted that the implant guide 210, with its associated accessories, may be used in a similar fashion.

During the procedure, an incision 300 may be made to gain access to the spinal column of the patient. In some embodiments, an access cannula, retractor, or other device (not shown) may be inserted into the incision 300 to maintain access to the vertebrae 2 during the medical procedure. In other embodiments, access to the vertebrae 2 may be maintained directly through the incision. Having gained access to the vertebrae 2 of the spinal column, a first vertebral anchor 100a may be secured to a first vertebra 2a and a second vertebral anchor 100b may be secured to a second vertebra 2b, such as an adjacent vertebra. For example, the vertebral anchors 100, in the form of pedicle screws, may be screwed into the pedicle region of the vertebrae 2, or other region of the vertebrae 2.

A first implant guide 310, which may be a rigid implant guide or a flexible implant guide like the implant guide 10, may be docked or engaged with the head portion 102 of the first vertebral anchor 100a. Docking of the implant guide 310 to the first vertebral anchor 100a may be accomplished using the docking technique described above regarding FIGS. 6A-6C, or docking of the implant guide 310 may be accomplished using another desired docking technique.

A second implant guide 10 may be docked or engaged with the head portion 102 of the second vertebral anchor 100b. Docking of the flexible implant guide 10 to the second vertebral anchor 100b may be accomplished using the docking technique described above regarding FIGS. 6A-6C, or docking of the implant guide 10 may be accomplished using another desired docking technique.

In some circumstances the vertebral anchors 100a, 100b may be placed in a converging angular relationship. A converging relationship of the vertebral anchors 100a, 100b may result in the shaft 314 of the first implant guide 310 converging toward the shaft 14 of the second implant guide 10 when the implant guides 10, 310 are docked with the vertebral anchors 100a, 100b. In some situations in which the shaft 314 of the first implant guide 310 is convergent toward the shaft 14 of the second implant guide 10, the implant guide 10 may be flexed away from the first implant guide 310 (shown by arrow in FIG. 10B), providing more clearance between the shaft 314 of the first implant guide 310 and the shaft 14 of the second implant guide 10. This added clearance may facilitate the insertion of one or more components of a vertebral stabilization system 4 to the spinal column.

Figure 10A:
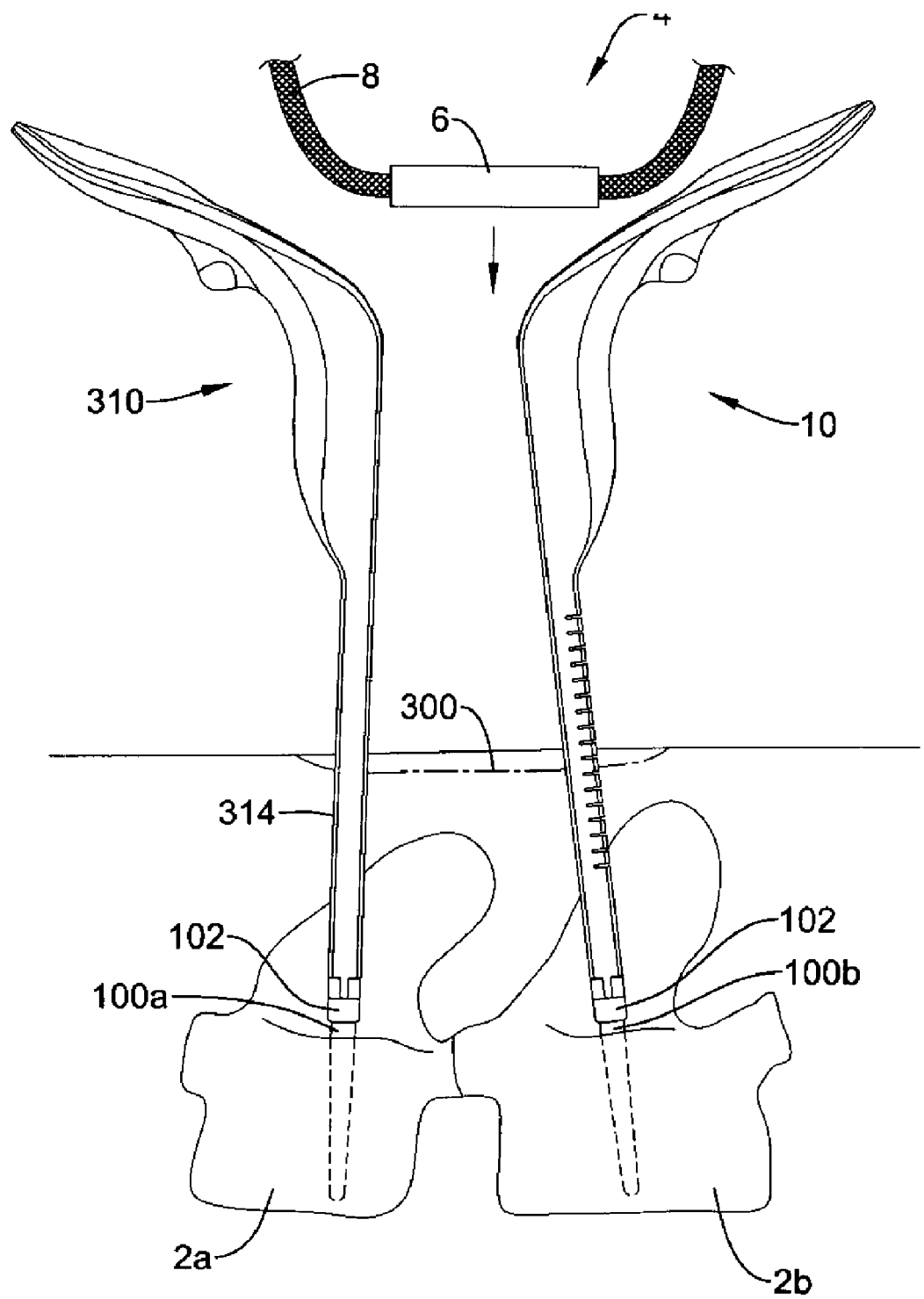
FIGS. 10A-10D illustrate an exemplary method of installing a spinal stabilization system with the implant guide of FIG. 1.
Figure 10B:
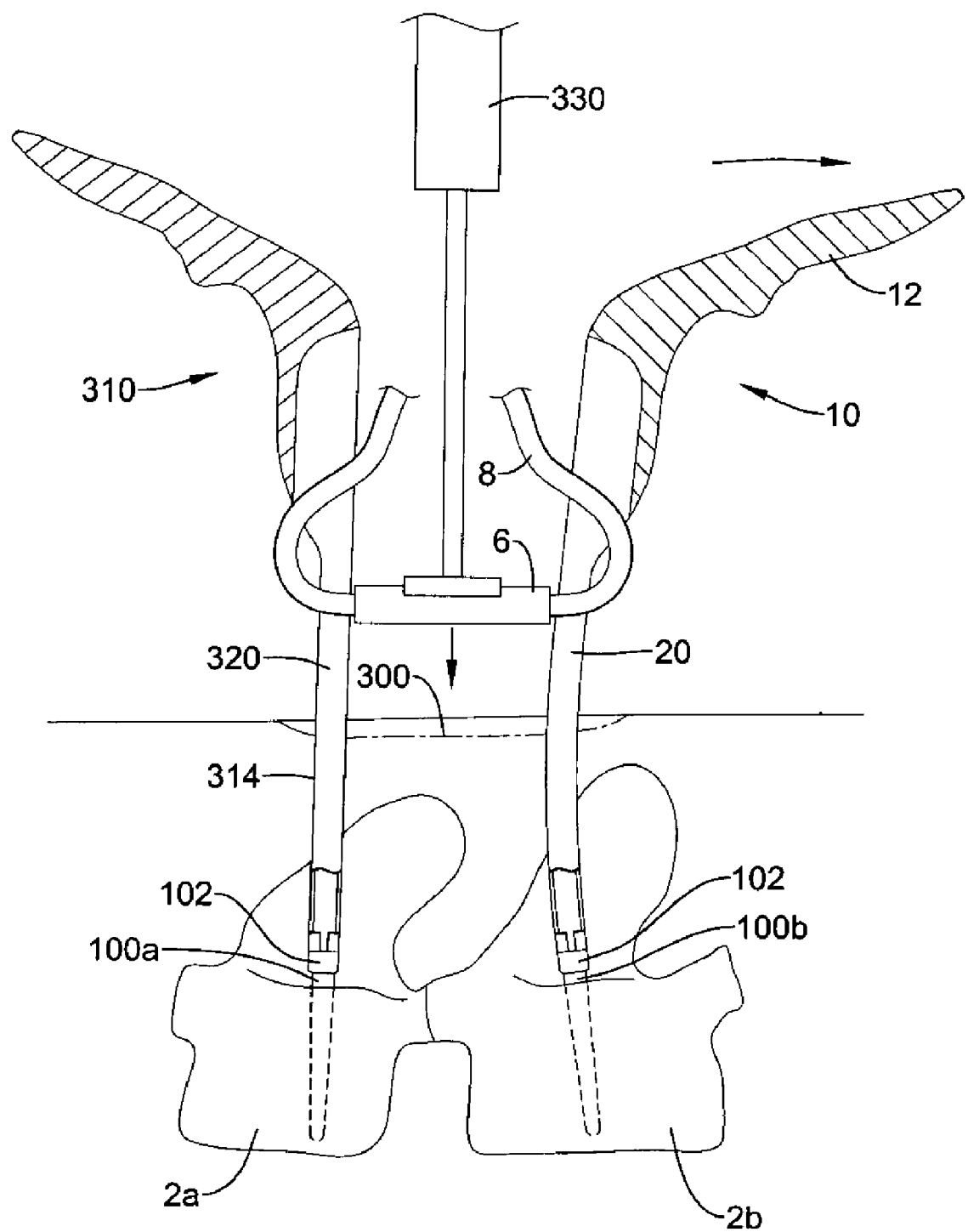

Additionally or alternatively, the implant guides 10, 310 may be used to distract the vertebrae 2 by applying a force to one or both of the implant guides 10, 310. The implant guide 10 may deflect, as shown in FIG. 10B when an applied force is applied to the handle 12 of the implant guide 10. In some embodiments, the implant guide 10 may be configured to withstand a predetermined amount of distractive force before deflecting. Thus, the shaft 14 of the implant guide 10 may be configured to be a distraction limiter, flexing once a threshold amount of distractive force is attained, thereby limiting the amount of force transferred to the vertebral anchor 100b by the implant guide 10.

In some embodiments, the stabilization insert 70 may be inserted along the shaft 14 of the implant guide 10, stabilizing the shaft 14 of the implant guide 10 in a singular configuration. For instance, the stabilization insert 70 may retain the shaft 14 of the implant guide 10 in a curved configuration or in a straight configuration, if desired. It is noted that at various times during the medical procedure, the stabilization insert 70 may be withdrawn and/or replaced with another stabilization insert, as desired, to alter the shape and/or flexibility bestowed on the shaft 14.

A vertebral stabilization system 4 to be secured to the vertebral anchors 100a, 100b may be introduced to the spinal column with the implant guides 10, 310. In some embodiments, the vertebral stabilization system 4 may include a first elongate member, which is shown in the form of a spacer 6, and/or a second elongate member, which is shown in the form of a flexible cord 8. The first and/or second elongate member may be directly and/or indirectly secured to the vertebral anchors 100a, 100b during the medical procedure. For instance, the flexible cord 8 may be disposed through an aperture of the spacer 6 exterior of the body of the patient and then advanced to the vertebral anchors 100a, 100b. In other embodiments, however, the flexible cord 8 may be disposed through an aperture of the spacer 6 after the cord 8 has been inserted into the incision 300 and/or secured to at least one of the vertebral anchors 100.

FIG. 10B illustrates one possible way of inserting components of the vertebral stabilization system 4 to the vertebral anchors 100a, 100b. With the spacer 6 disposed on the cord 8, a first portion of the cord 8 may be positioned in the channel 320 of the shaft 314 of the first implant guide 310, and a second portion of the cord 8 may be positioned in the channel 20 of the shaft 14 of the second implant guide 10. The channel 320 of the first implant guide 310 may be aligned with and in communication with the channel 128 in the head portion 102 of the first vertebral anchor 100a, and the channel 20 of the second implant guide 10 may be aligned with and in communication with the channel 128 in the head portion 102 of the second vertebral anchor 100b. The channels 20, 320 of the implant guides 10, 320 may help guide the cord 8 into proper position in the channels 128 of the vertebral anchors 100a, 100b.

The spacer 6 may be positioned between the shaft 314 of the first implant guide 310 and the shaft 14 of the second implant guide 10. A pusher member 330, coupled to the spacer 6, may be used to advance the vertebral stabilization system 4 to the vertebral anchors 100a, 100b. The flexible nature of the implant guide 10 may help guide the spacer 6 into proper alignment between the vertebral anchors 100a, 100b. For instance, the shaft 14 of the implant guide 10 may be flexed away from the shaft 314 of the first implant guide 310 to allow the spacer 6 to be positioned between the shaft 314 of the first implant guide 310 and the shaft 14 of the second implant guide 10.

Figure 10C:
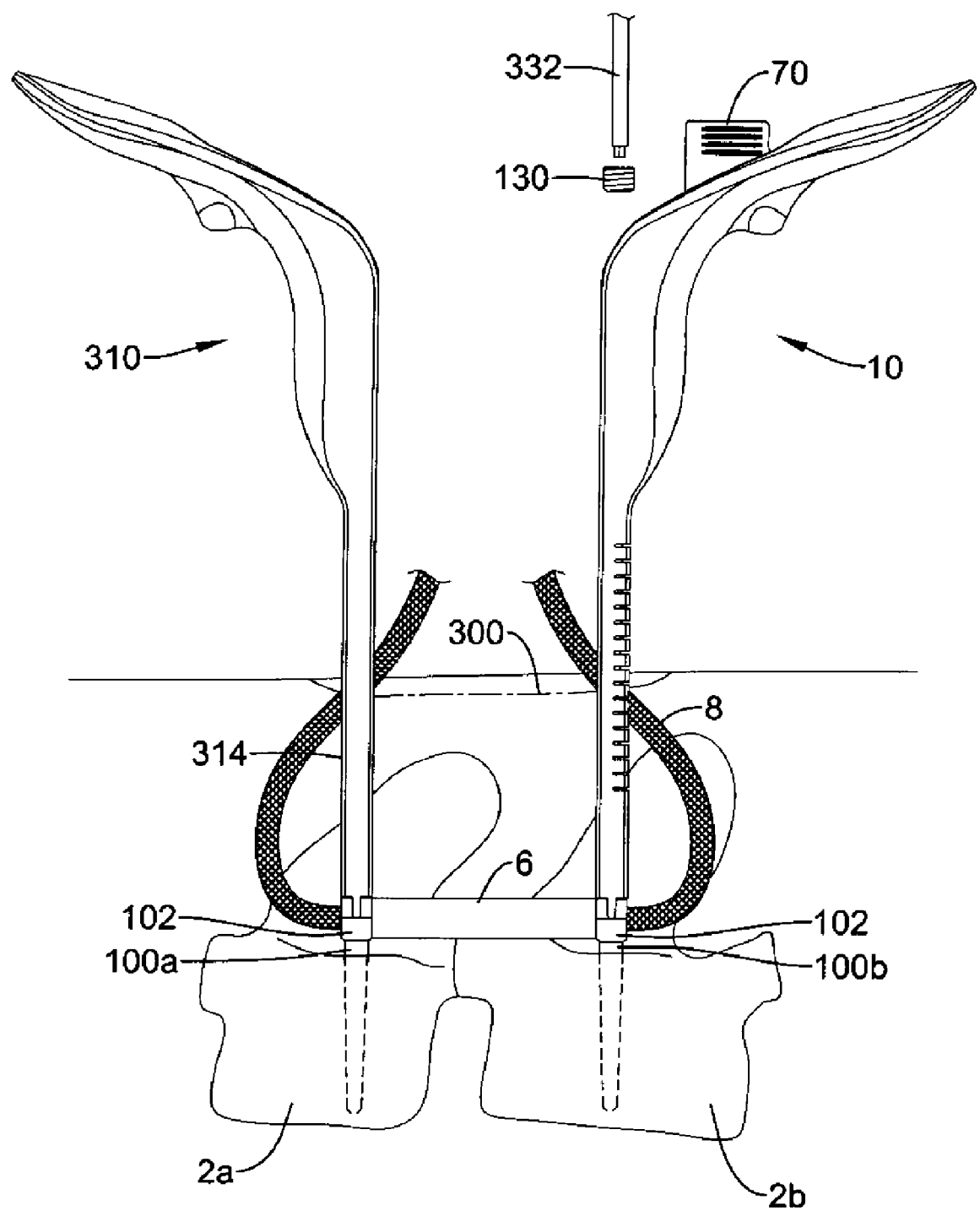

FIG. 10C illustrates the spacer 6 in proper alignment between the head portions 102 of the vertebral anchors 100a, 100b, and the flexible cord 8 extending through the channel 128 of the head portions 102 of each of the vertebral anchors 100a, 100b, with excess portions of the cord 8 extending external of the incision 300. In some embodiments as shown in FIG. 10C, the spacer 6 may provide some degree of distraction between the vertebrae 2 when properly positioned between the vertebral anchors 100a, 100b.

A stabilization insert 70 may be inserted along the shaft 14 of the implant guide 10 to stabilize the shaft 14 to a desired configuration, such as a straight configuration shown in FIG. 10C. A threaded fastener 130, such as a set screw, may be advanced along the shaft 14 through the channel 84 of the stabilization insert 70 toward the head portion 102 of the vertebral fastener 100b. A driver 332 may be used to rotate the threaded fastener 130 in order to screw the threaded fastener 130 into threaded engagement with the threaded opening 108 of the vertebral anchor 100b, securing the flexible cord 8, or other elongate member of the vertebral stabilization system 4, to the head portion 102 of the vertebral anchor 100*b*.

The cord 8 may then be tensioned to a desired amount of tensile force between the first vertebral anchor 100*a* and the second vertebral anchor 100*b*. For instance, a tensioning instrument, such as a tensioning instrument shown and described in U.S. patent application Ser. Nos. 11/737,151 and 12/025,984, the disclosures of which are incorporated herein by reference, may be used to apply a desired amount of tension to the cord 8. With the cord 8 held in tension, another threaded fastener 130 may be threadably engaged in the threaded opening 108 of the vertebral anchor 100*a* to secure the flexible cord 8, or other elongate member of the vertebral stabilization system 4, to the head portion 102 of the vertebral anchor 100*a*.

Figure 10D:
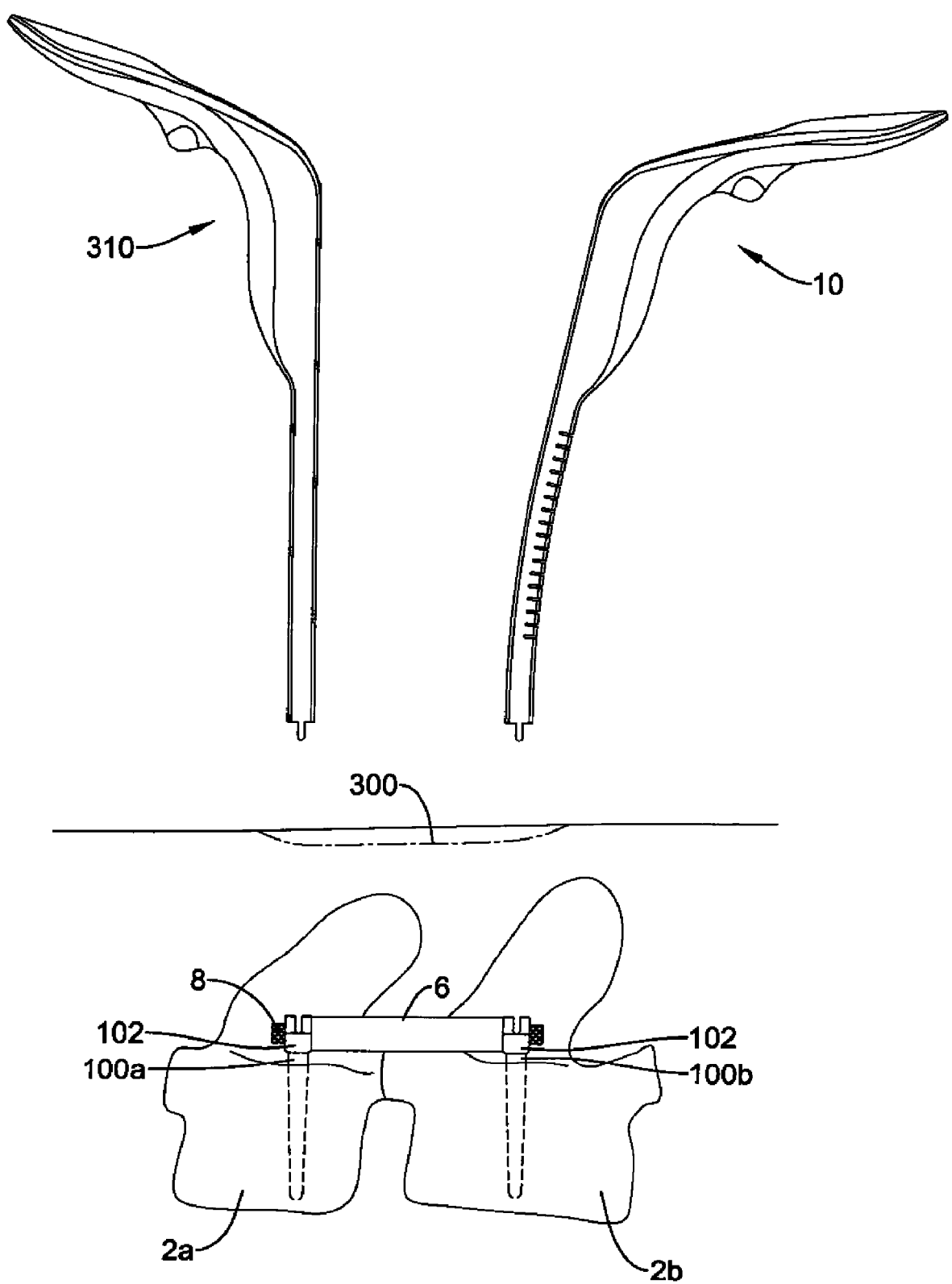

Once the vertebral stabilization system 4 is secured to the vertebral anchors 100*a*, 100*b*, the implant guides 10, 310 may be undocked or disengaged from the heads 102 of the vertebral anchors 100*a*, 100*b* and removed from the patient as shown in FIG. 10D. The excess lengths of the cord 8 may be trimmed and the incision 300 may be closed to complete the installation.

It is noted that variations of the above described surgical technique for installing a vertebral stabilization system 4 may be performed, as desired. For example, U.S. patent application Ser. Nos. 11/539,287, 11/737,151, 11/743,481, and 12/025,984, the disclosures of which are incorporated herein by reference, demonstrate some surgical techniques for installing a vertebral stabilization system which may be modified in view of the present disclosure.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A system for implantation of a spinal stabilization system comprising:
    an implant guide including a handle and a shaft extending from the handle, a distal end of the shaft configured for engagement with a head portion of a vertebral anchor, the shaft having flexibility characteristics allowing the shaft to flexibly bend between a first equilibrium configuration and a second deflected configuration; and
    an insert slidably disposed along the shaft of the implant guide to subject the shaft to the second configuration, wherein the insert inhibits the shaft from bending from the second configuration to the first configuration; and
    wherein the shaft of the implant guide includes a first leg spaced from a second leg, wherein the insert is slidably disposed between the first leg and the second leg; and
    wherein the insert includes a first rail slidably engaged with a slot extending along the first leg of the shaft, and the insert includes a second rail slidably engaged with a slot extending along the second leg of the shaft.

2. The system of claim 1, wherein the insert includes a curved shaft portion along a length of the insert having a curvature.

3. The system of claim 1, wherein the first configuration is a configuration in which a length of the shaft is straight, and the second configuration is a configuration in which the length of the shaft is curved.

4. The system of claim 1, wherein the first configuration is a configuration in which a length of the shaft is curved, and the second configuration is a configuration in which the length of the shaft is straight.

5. The system of claim 1, wherein the insert is a docking member configured to assist in docking the implant guide to a head portion of a vertebral anchor.

6. The system of claim 1, wherein the flexibility characteristics of the shaft include a plurality of slots formed in a portion of the shaft.

7. A system for use in the installation of a spinal stabilization system comprising:
    a vertebral anchor including a head portion and a shaft portion, the head portion including a threaded opening extending into the head portion from an upper end of the head portion;
    an implant guide including a handle and a shaft extending from the handle, a distal end of the shaft configured for engagement with the head portion of the vertebral anchor; and
    a docking member inserted along the shaft of the implant guide, a distal end of the docking member including a post sized for insertion into the threaded opening of the head portion of the vertebral anchor;
    the shaft and the handle of the implant guide being slidable relative to the docking member such that in a first configuration the distal end of the shaft is disengaged from the head portion of the vertebral anchor while the post of the docking member is positioned in the threaded opening of the vertebral anchor, and in a second configuration the distal end of the shaft is engaged with the head portion of the vertebral anchor while the post of the docking member is positioned in the threaded opening of the vertebral anchor.

8. The system of claim 7, wherein the shaft includes a slot and the docking member includes a rail slidably disposed in the slot of the shaft.

9. The system of claim 7, wherein the docking member includes a slot and the shaft includes a rail slidably disposed in the slot of the docking member.

10. The system of claim 7, wherein the shaft includes a first leg spaced from a second leg, wherein the docking member is disposed between the first leg and the second leg.

11. The system of claim 10, wherein the first leg includes a first slot and the second leg includes a second slot, and
    wherein the docking member includes a first rail slidably disposed in the first slot and a second rail slidably disposed in the second slot.

12. The system of claim 7, wherein the distal end of the shaft includes a first projection and a second projection, and the head portion of the vertebral anchor includes a first opening and a second opening;
    wherein in the second configuration the first projection is positioned in the first opening and the second projection is positioned in the second opening.

13. The system of claim 7, further including verification means for verifying when the shaft is positioned in the second configuration.

14. A method of engaging a vertebral anchor with an implant guide, the method comprising:
    providing a docking member having a proximal portion and a distal portion;
    engaging the distal portion of the docking member with a head portion of a vertebral anchor implanted into a bone of a spinal column;
    with the distal portion of the docking member engaged with the head portion of a vertebral anchor, sliding an implant guide along the docking member toward the head portion of the vertebral anchor;

engaging a distal end of the implant guide with the head portion of the vertebral anchor while the distal portion of the docking member remains engaged with the head portion of the vertebral anchor; and disengaging the distal portion of the docking member from the head portion of the vertebral anchor once the distal end of the implant guide is engaged with the head portion of the vertebral anchor.

15. The method of claim 14, wherein implant guide includes a handle and a shaft extending from the handle, the shaft including a first leg and a second leg;

wherein the docking member is slidably disposed between the first leg and the second leg of the shaft of the implant guide.

16. The method of claim 14, wherein the distal portion of the docking member includes a post, wherein engaging the distal portion of the docking member with the head portion of the vertebral anchor includes inserting the post of the docking member into a threaded opening of the head portion of the vertebral anchor.

* * * * *